US012427035B2

United States Patent
MacMillan et al.

(10) Patent No.: US 12,427,035 B2
(45) Date of Patent: Sep. 30, 2025

(54) INTERBODY SPACER FOR SPINAL FUSION

(71) Applicant: CoreLink, LLC, St. Louis, MO (US)

(72) Inventors: Adam MacMillan, Quincy, MA (US); Josh Arnone, St. Charles, MO (US)

(73) Assignee: CORELINK, LLC, St. Louis, MO (US)

( * ) Notice: Subject to any disclaimer, the term of this patent is extended or adjusted under 35 U.S.C. 154(b) by 206 days.

(21) Appl. No.: 18/317,900

(22) Filed: May 15, 2023

(65) Prior Publication Data

US 2023/0301795 A1   Sep. 28, 2023

Related U.S. Application Data

(63) Continuation of application No. 17/031,090, filed on Sep. 24, 2020, now abandoned.

(60) Provisional application No. 62/905,123, filed on Sep. 24, 2019.

(51) Int. Cl.
*A61F 2/44* (2006.01)
*A61F 2/30* (2006.01)
*A61F 2/46* (2006.01)

(52) U.S. Cl.
CPC .......... *A61F 2/4455* (2013.01); *A61F 2/3094* (2013.01); *A61F 2/442* (2013.01); *A61F 2/4611* (2013.01); *A61F 2002/30985* (2013.01)

(58) Field of Classification Search
CPC . A61B 17/70–7098; A61B 17/72–7291; A61F 2/4611
See application file for complete search history.

(56) References Cited

U.S. PATENT DOCUMENTS

| | | |
|---|---|---|
| 8,114,082 B2 | 2/2012 | Boyajian et al. |
| 8,361,155 B2 | 1/2013 | Lambrecht et al. |
| 8,454,612 B2 | 6/2013 | Lambrecht et al. |
| 9,017,412 B2 | 4/2015 | Wolters et al. |
| 9,351,847 B2 | 5/2016 | Reed et al. |
| 9,504,584 B1 | 11/2016 | Stein et al. |
| 9,517,144 B2 | 12/2016 | McAtamney et al. |
| 9,872,780 B2 | 1/2018 | Reed et al. |
| 10,098,755 B2 | 10/2018 | Kaufmann et al. |
| 10,245,157 B2 | 4/2019 | Chataigner et al. |
| 2003/0078668 A1 | 4/2003 | Michelson |
| 2005/0059972 A1* | 3/2005 | Biscup ............... A61B 17/7061 606/907 |

(Continued)

FOREIGN PATENT DOCUMENTS

WO   2012121726 A1   9/2012

OTHER PUBLICATIONS

International Search Report and Written Opinion received for PCT Application Serial No. PCT/US2020/052455 dated Feb. 1, 2021, 11 pages.

*Primary Examiner* — Nicholas J Plionis
(74) *Attorney, Agent, or Firm* — Stinson LLP

(57) ABSTRACT

An interbody spacer for spinal fusion surgery includes a body configured for insertion within an interbody space between two adjacent vertebrae. The body defines at least one fastener-receiving opening for receiving a fastener for securing the body within the interbody space. A blocking member is disposable in the fastener-receiving opening for preventing the fastener from being withdrawn from the fastener-receiving opening once the fastener has been fully inserted into the fastener-receiving opening.

14 Claims, 21 Drawing Sheets

(56) References Cited

U.S. PATENT DOCUMENTS

| | | | |
|---|---|---|---|
| 2007/0161985 A1* | 7/2007 | Demakas | A61B 17/7032 |
| | | | 606/301 |
| 2011/0230971 A1 | 9/2011 | Donner et al. | |
| 2012/0232599 A1 | 9/2012 | Schoenly et al. | |
| 2012/0271362 A1* | 10/2012 | Martineau | B22F 7/008 |
| | | | 470/9 |
| 2013/0253590 A1 | 9/2013 | Blain | |
| 2014/0194877 A1* | 7/2014 | Mangiardi | A61L 31/148 |
| | | | 606/62 |
| 2014/0228959 A1 | 8/2014 | Niemiec et al. | |
| 2014/0277456 A1 | 9/2014 | Kirschman | |
| 2015/0057754 A1 | 2/2015 | Reed et al. | |
| 2016/0074171 A1 | 3/2016 | Muller et al. | |
| 2016/0151171 A1 | 6/2016 | Mozeleski et al. | |
| 2016/0157908 A1* | 6/2016 | Cawley | A61F 2/3094 |
| | | | 606/301 |
| 2016/0324652 A1 | 11/2016 | Brow | |
| 2018/0177606 A1 | 6/2018 | Reed | |
| 2018/0303623 A1 | 10/2018 | Shoshtaev | |
| 2018/0318100 A1 | 11/2018 | Altarac et al. | |
| 2019/0046329 A1 | 2/2019 | Padovani et al. | |
| 2019/0105174 A1 | 4/2019 | Kaufmann et al. | |

* cited by examiner

FIG. 16A
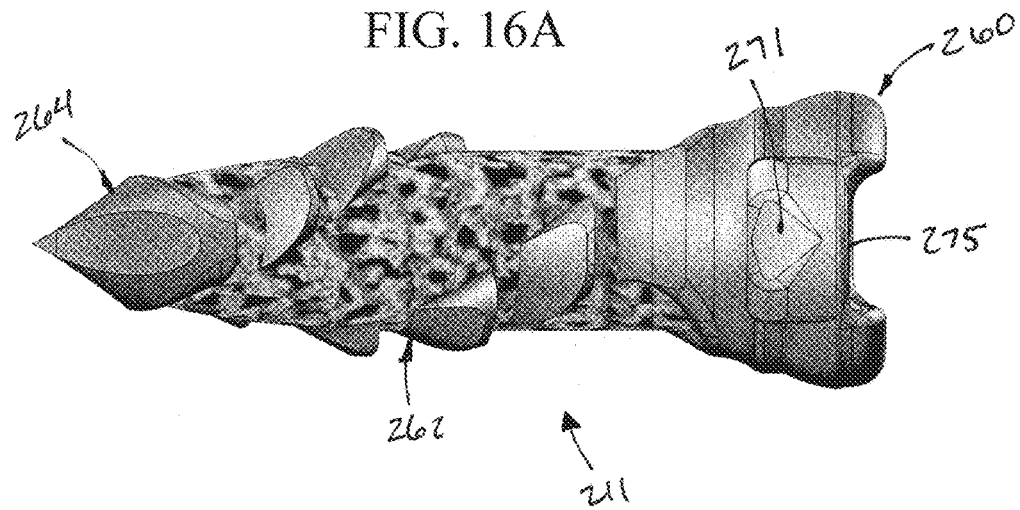
FIG. 16B
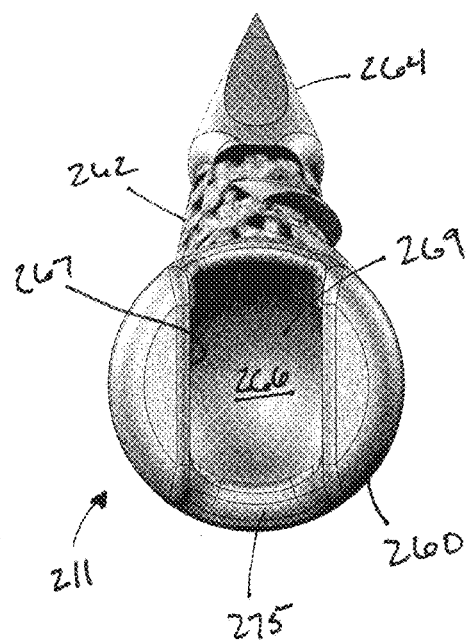
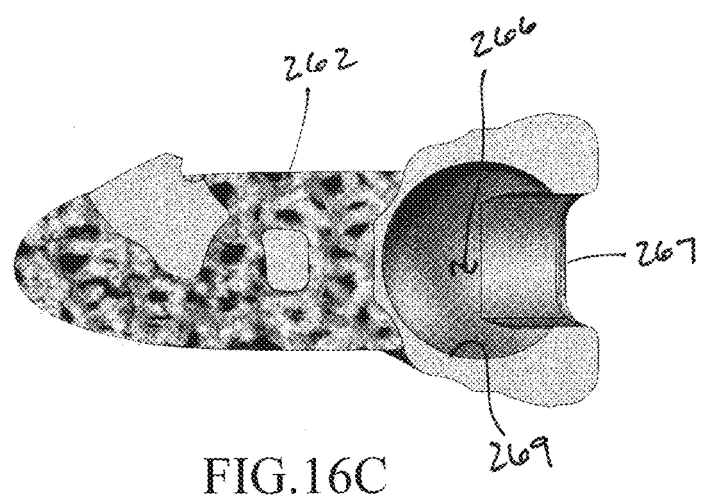
FIG. 16C

INTERBODY SPACER FOR SPINAL FUSION

CROSS-REFERENCE TO RELATED APPLICATION

This application is a continuation of U.S. application Ser. No. 17/031,090 filed Sep. 24, 2020, which claims priority to U.S. Provisional Patent Application Ser. No. 62/905,123, filed Sep. 24, 2019, which is hereby incorporated by reference in its entirety.

FIELD OF THE DISCLOSURE

The present disclosure generally relates to an interbody spacer for spinal fusion.

BACKGROUND OF THE DISCLOSURE

Spinal fusion is a surgical procedure used to correct problems with vertebrae of the spine. Spinal fusion fuses together the painful vertebrae so that they heal into a single, solid bone. In one method, the intervertebral disc between two vertebrae is removed and a small interbody spacer, also known as a cage, is inserted between the vertebrae. These interbody spacers usually contain bone graft material to promote bone healing and facilitate the fusion. After the interbody spacer is inserted, surgeons often use metal screws, plates, and rods to further stabilize the spine.

SUMMARY

In one aspect, an interbody spacer for spinal fusion surgery generally comprises a body configured for insertion within an interbody space between two adjacent vertebrae. The body defines at least one fastener-receiving opening for receiving a fastener for securing the body within the interbody space. A blocking member is disposable in the fastener-receiving opening for preventing the fastener from being withdrawn from the fastener-receiving opening once the fastener has been fully inserted into the fastener-receiving opening.

In another aspect, a method of making an interbody spacer for spinal fusion surgery generally comprises 3D printing the interbody spacer. The interbody spacer comprising a body and a blocking member movable relative to the body.

In yet another aspect, a fastener for use in an interbody spacer for spinal fusion surgery generally comprises a base defining a receptacle for receiving a driver for driving the fastener into a bony structure. A shaft extends from the base along an arc. A tip portion extends from the shaft and includes a pointed end for taping into the bony structure.

BRIEF DESCRIPTION OF THE DRAWINGS

FIG. 16A is a side view of another fastener;

FIG. 16B is an end view of the fastener of FIG. 16A;

FIG. 16C is a section of the fastener of FIG. 16A;

Corresponding reference characters indicate corresponding parts throughout the drawings.

DETAILED DESCRIPTION OF THE DISCLOSURE

Figure 1:
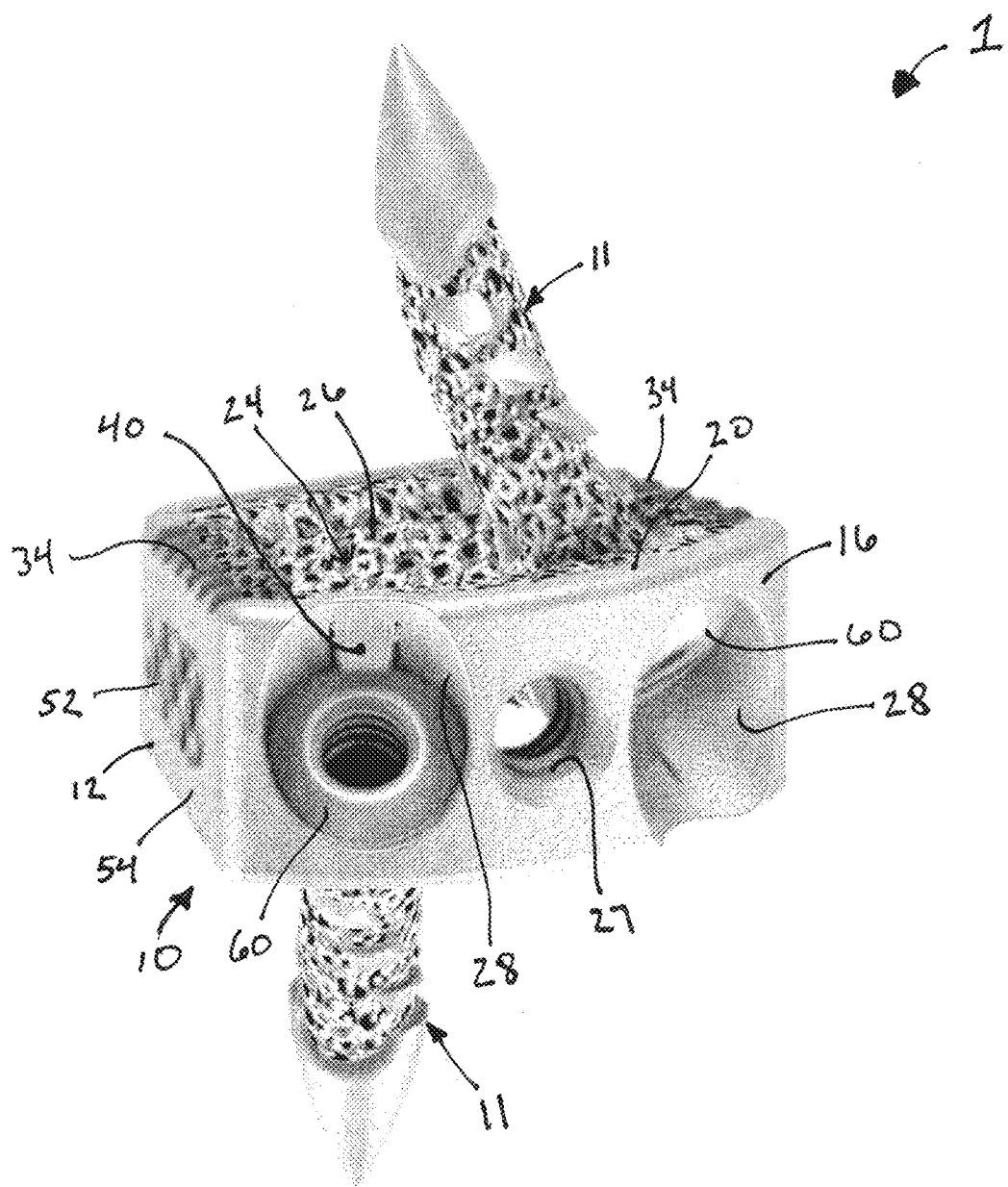
FIG. 1 is a perspective of one embodiment of an interbody spacer assembly constructed according to the teachings of the present disclosure.
Figure 2A:
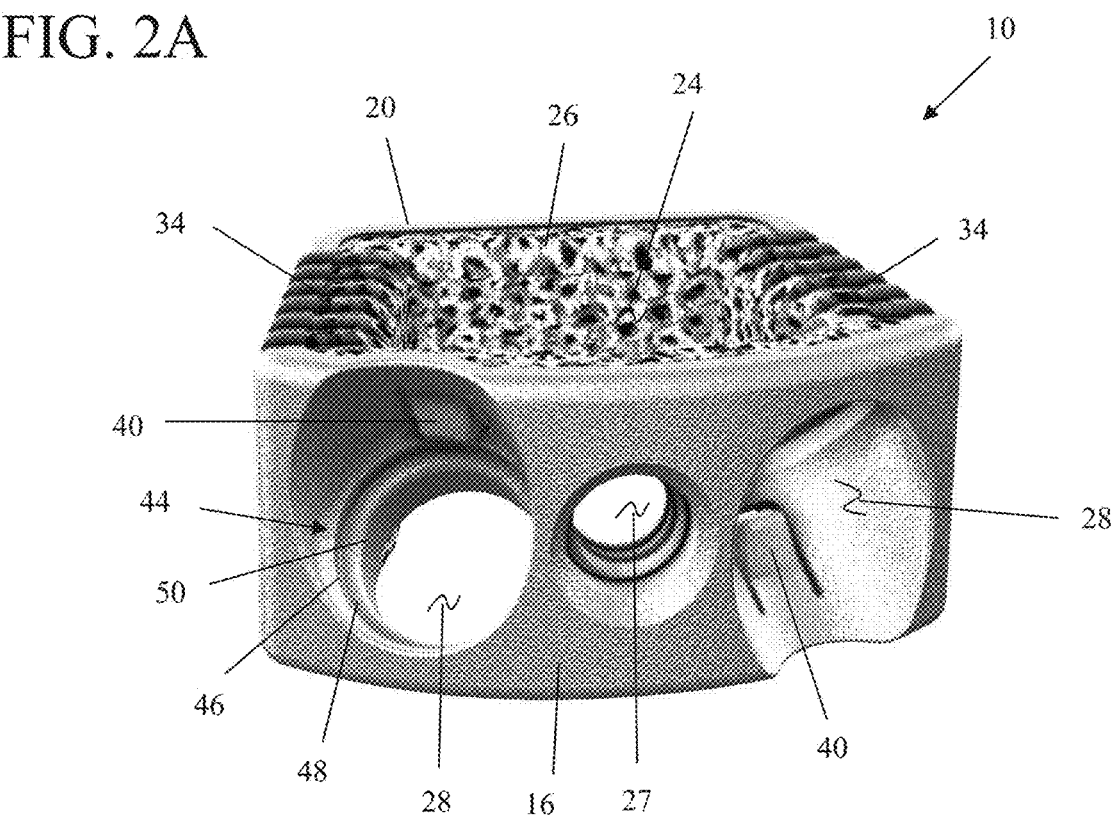
FIG. 2A is a perspective of an interbody spacer of the interbody spacer assembly.
Figure 2B:
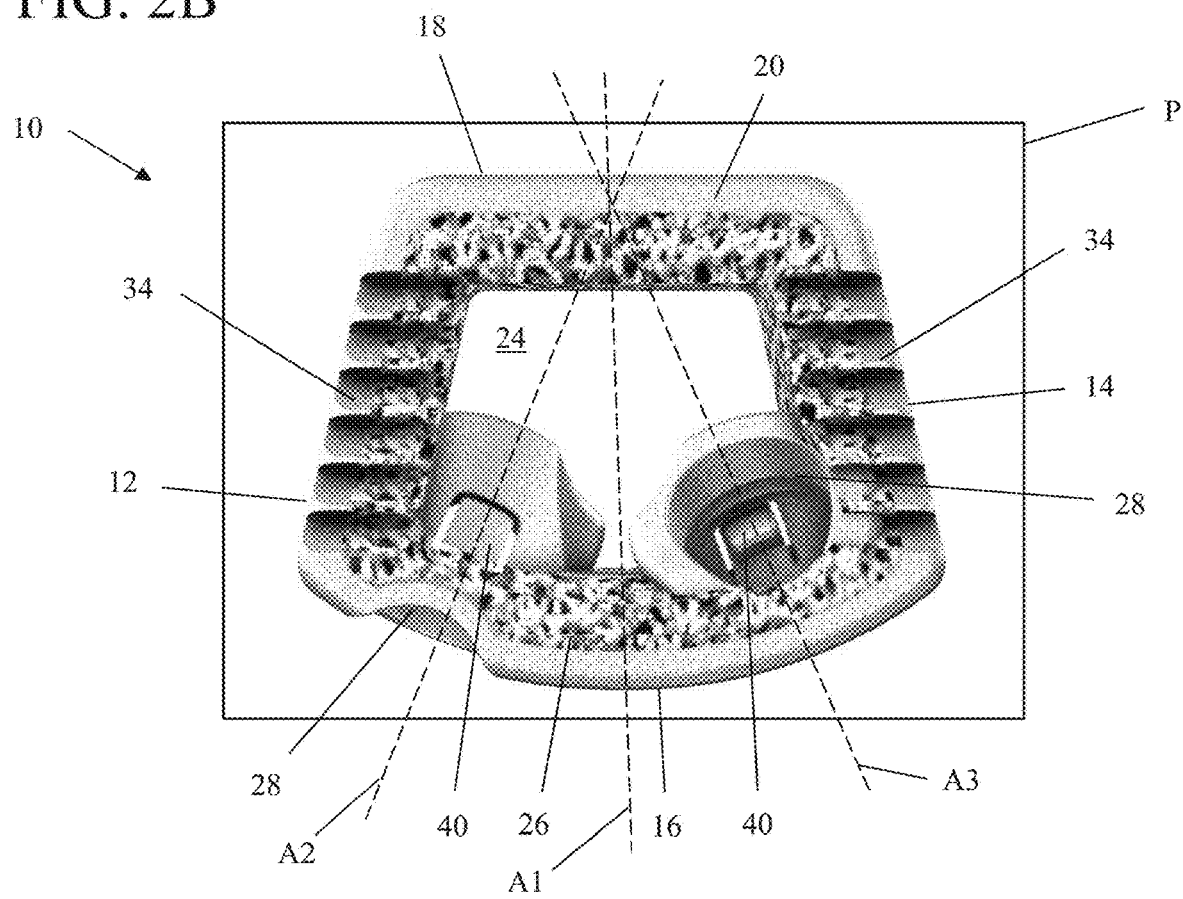
FIG. 2B is a top plan view of the interbody spacer.

Referring to FIGS. 1-2B of the drawings, a first embodiment of an interbody spacer assembly is generally indicated at reference numeral 1. The interbody spacer assembly 1 comprises an interbody spacer 10 and fasteners 11 for securing the spacer to one or more adjacent bony structures. The interbody spacer 10 is designed for use in lumbar interbody fusion surgery. The spacer 10 includes opposite first and second side walls generally indicated at 12, 14; opposing front and rear walls, generally indicated at 16 and 18, respectively, and extending between the first and second side walls and defining a transverse dimension (e.g., width) of the interbody spacer therebetween; and opposite upper and lower faces, generally indicated at 20, 22, defining a height of the interbody spacer therebetween. A horizontal plane P extends through the first and second side walls 12, 14 and the opposing front and rear walls 16, 18. Interior surfaces of the front and rear walls 16, 18 and the first and second side walls 12, 14 define an interior cavity 24. The upper and lower faces 20, 22 extend only partially across the upper and lower margins of the interbody spacer 10 defining openings at the top and bottom of the interbody spacer. Thus, the interior cavity 24 is open at upper and lower margins of the interbody spacer 10. The interior cavity, or "graft window," 24 is configured to receive bone graft material (not shown) to facilitate bone growth. In one embodiment, the graft window 24 is lined with an open-cell metal foam 26 (also referred to as a randomized "trabecular lattice" and may be comprised of titanium or other metal). The trabecular lattice 26 may extend along the entire heights and widths of the interior surfaces of the side walls 12, 14 and the front and rear walls 16, 18 (i.e., the lattice covers entireties of the interior surfaces of the side walls and front and rear walls). As used herein, terms such as "inner," "outer," "inward," "outward," "exterior," and "interior," relate to locations relative to the interior cavity, and the terms such as "front," "rear," "upper" and "lower" refer to the orientation of the spacer when positioned in the body.

Figure 8:
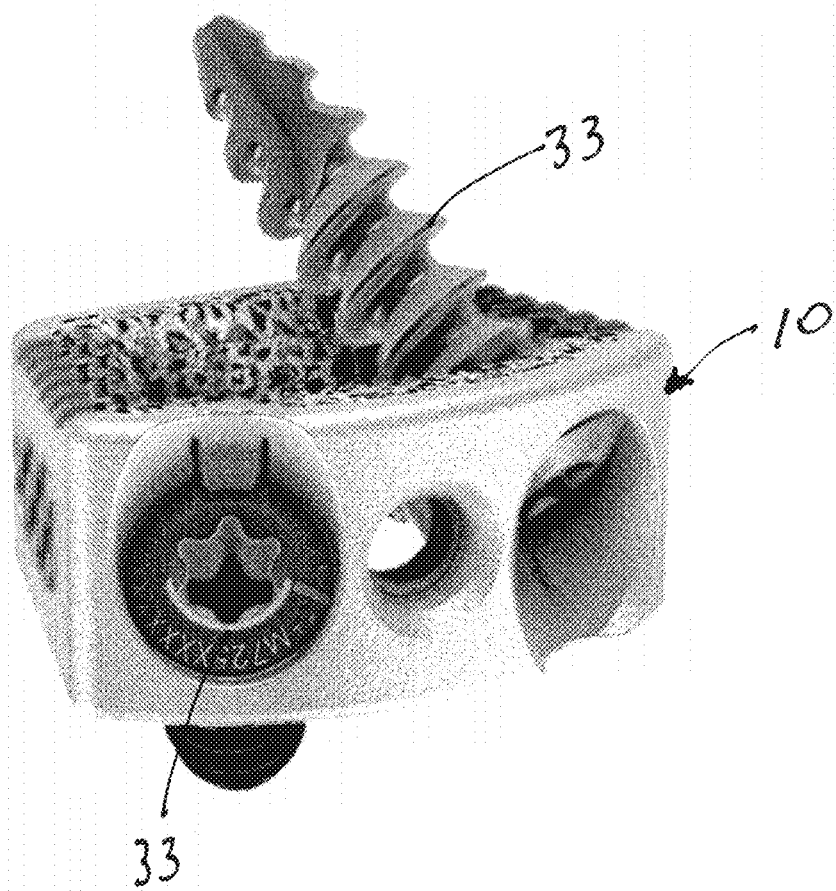
FIG. 8 is a perspective of the interbody spacer with another embodiment of fasteners.
Figure 9A:
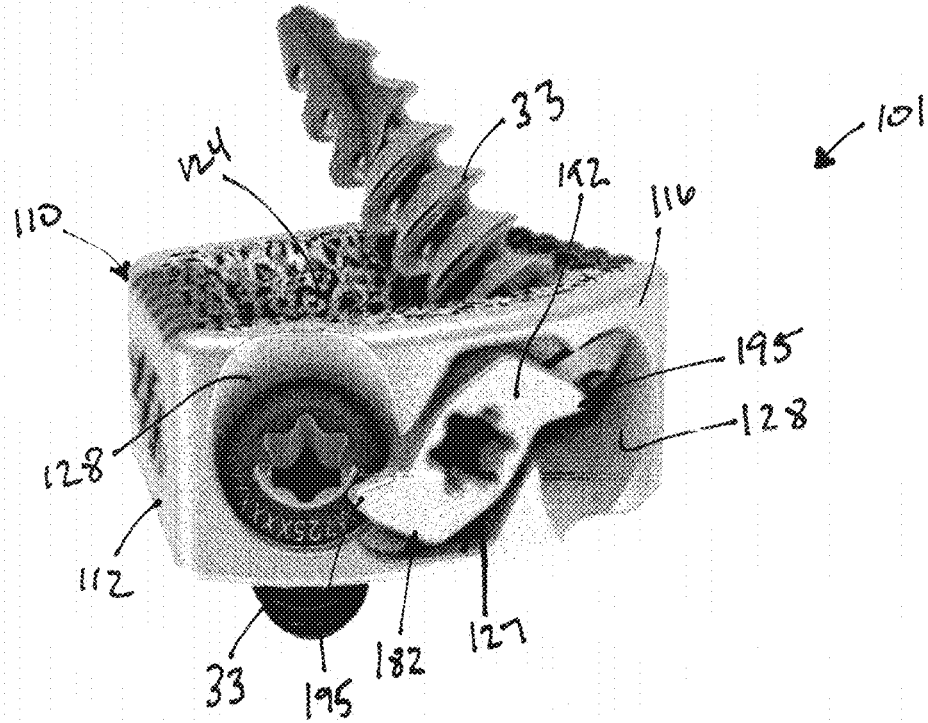
FIG. 9A is a front perspective of another embodiment of an interbody spacer assembly constructed according to the teachings of the present disclosure and showing a blocking member in a locked configuration.
Figure 9B:
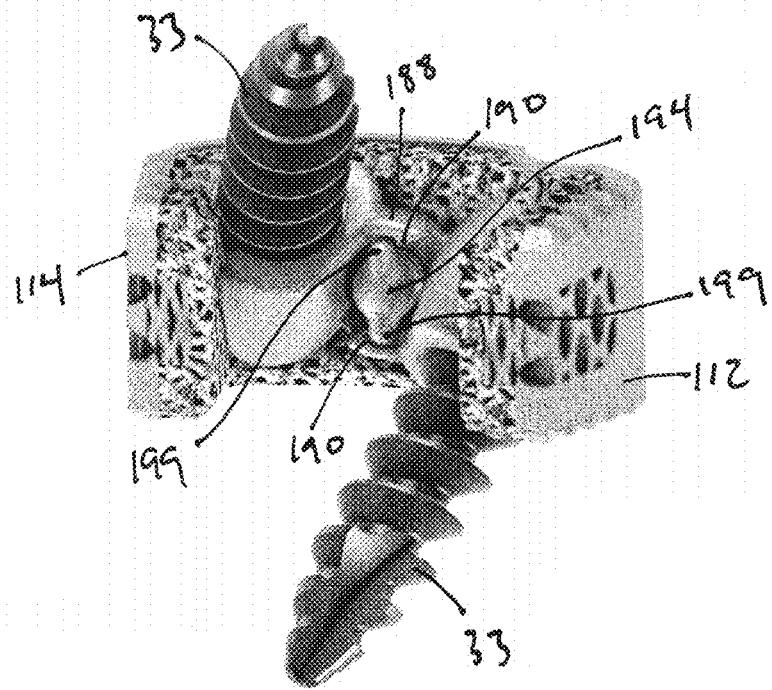
FIG. 9B is a fragmentary rear perspective of the assembly of FIG. 9A.
Figure 10A:
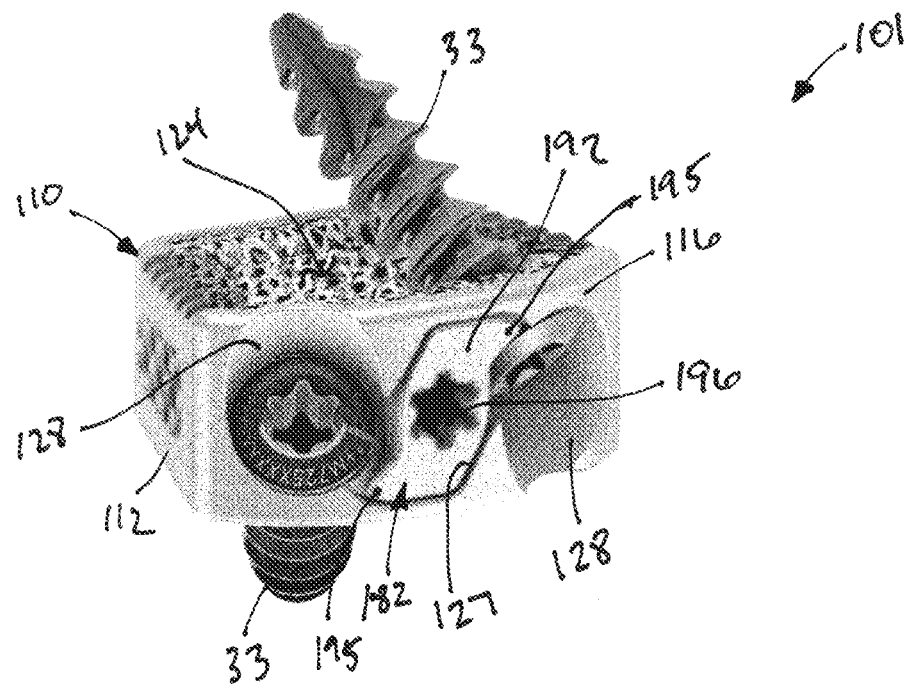
FIG. 10A is a front perspective of the interbody spacer assembly of FIG. 9A showing the blocking member in an unlocked configuration.
Figure 10B:
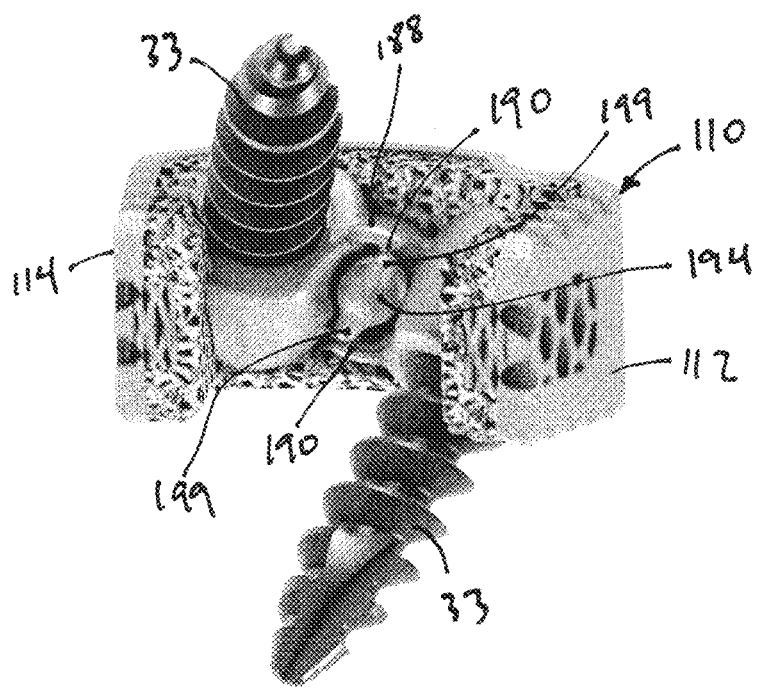
FIG. 10B is a fragmentary rear perspective of the assembly of FIG. 10A.
Figure 11:
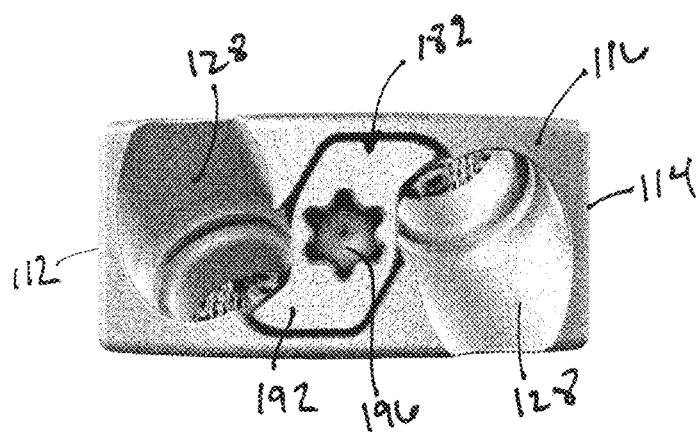
FIG. 11 is a top plan view of an interbody spacer of the assembly of FIG. 9A.
Figure 12:
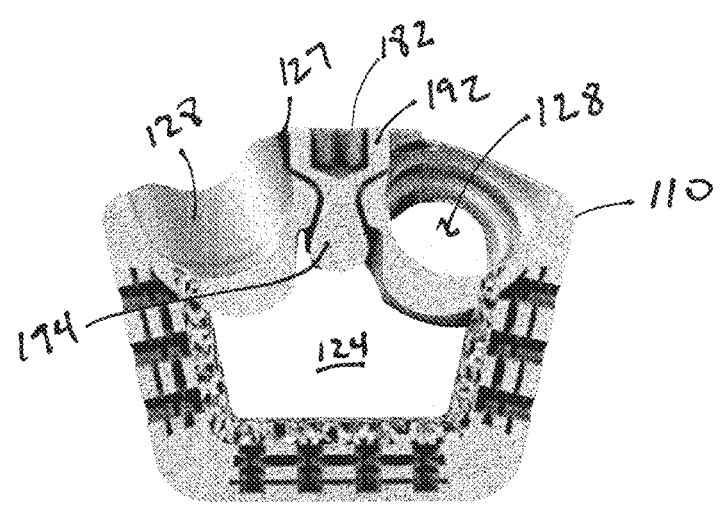
FIG. 12 is a section of the interbody spacer of FIG. 11.
Figure 13:
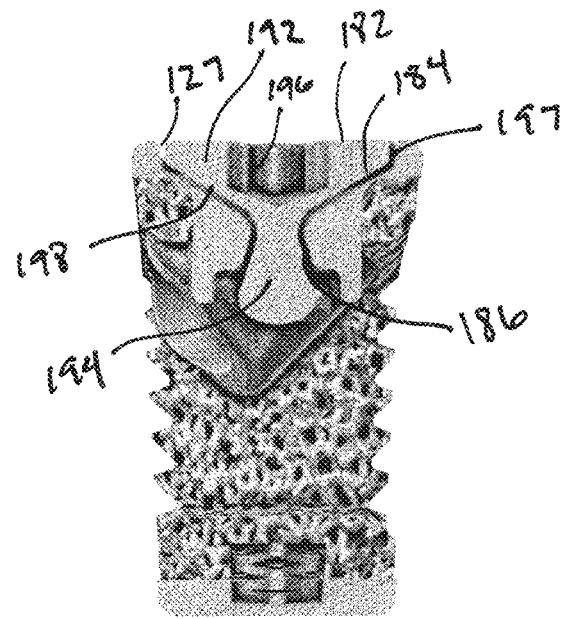
FIG. 13 is another section of the interbody spacer of FIG. 11.
Figure 14:
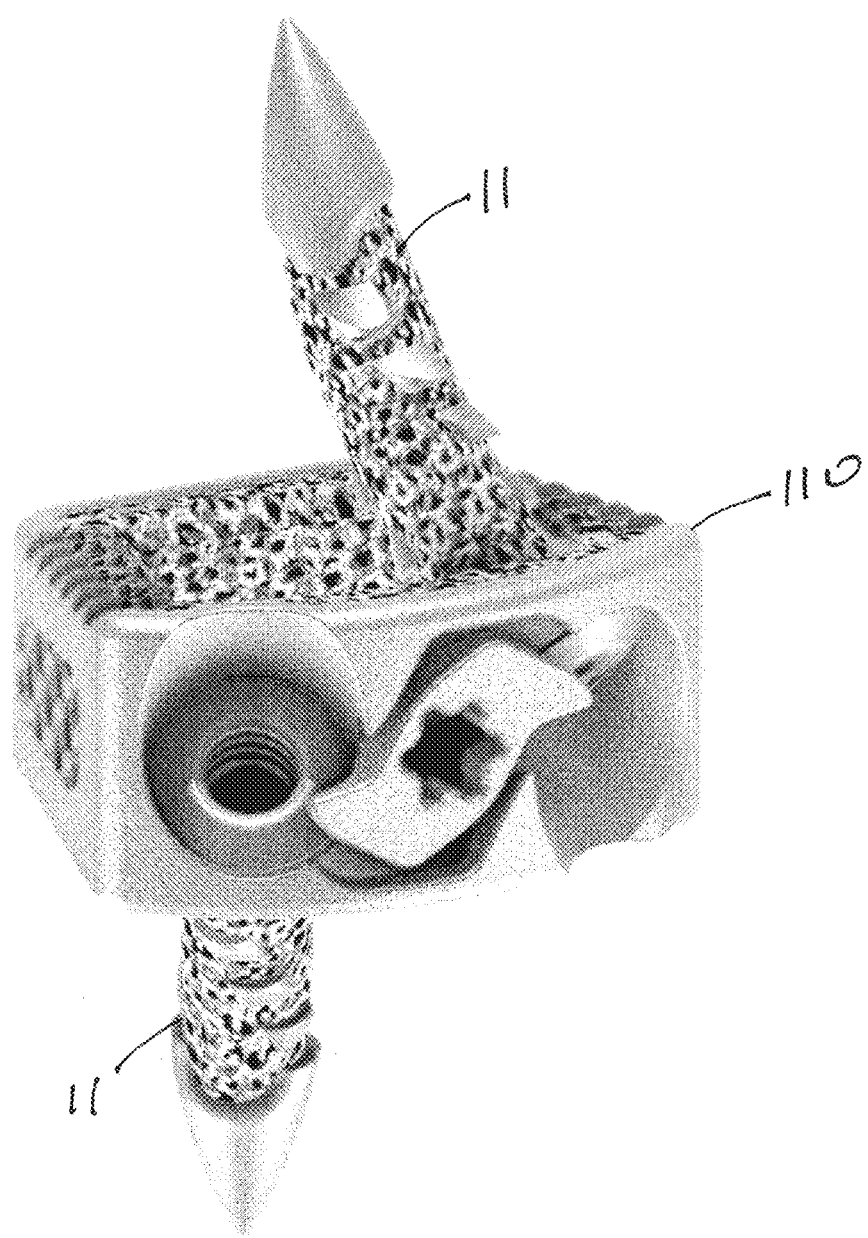
FIG. 14 is a perspective of the interbody spacer assembly of FIG. 9A with a different embodiment of fasteners.
Figure 15:
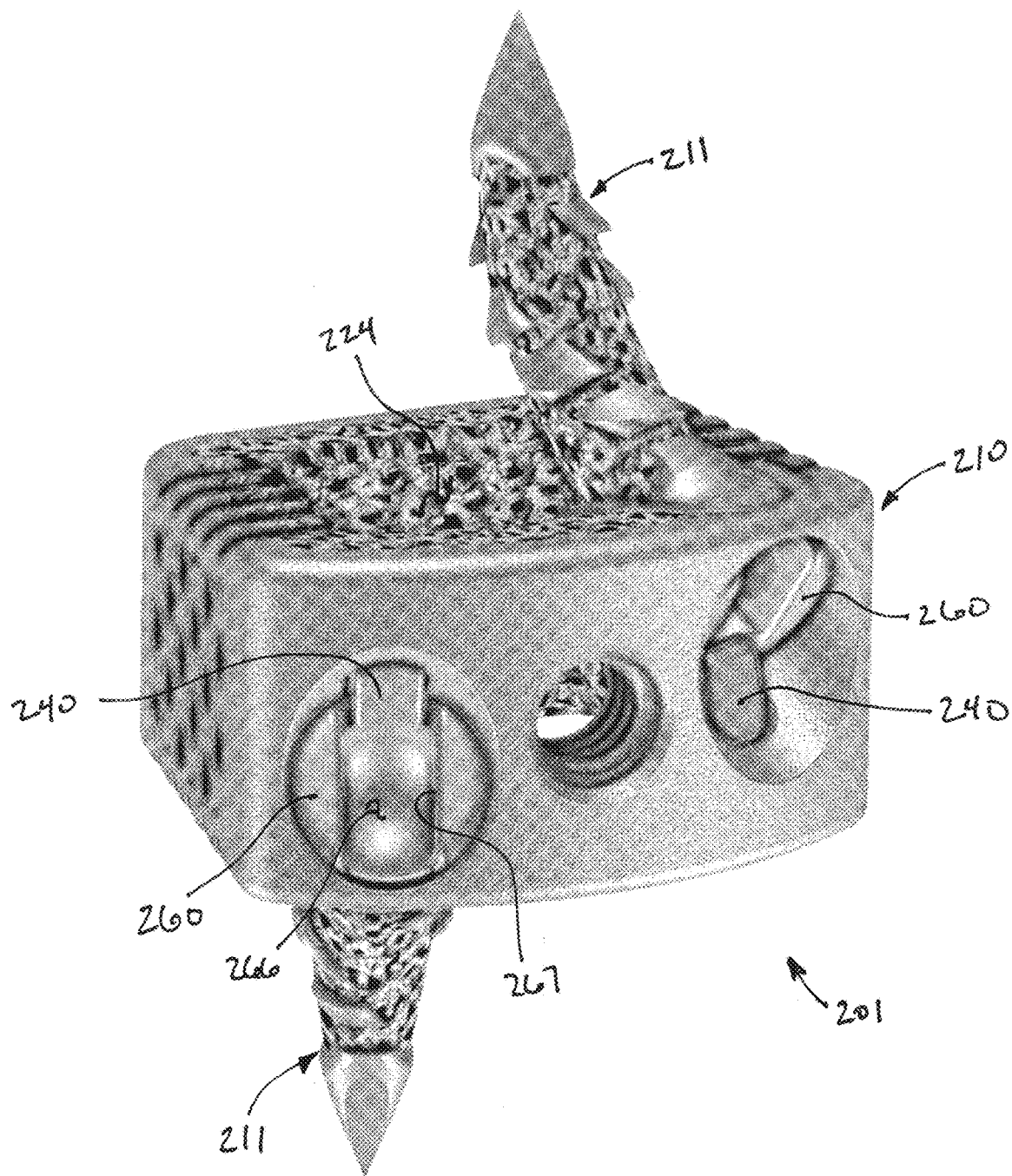
FIG. 15 is a front perspective of another embodiment of an interbody spacer assembly constructed according to the teachings of the present disclosure.

The first and second side walls 12, 14 and the front and rear walls 16, 18 comprise generally solid bodies (e.g., titanium or other metal or other material) to enhance the structurally integrity (e.g., compressive strength) of the spacer 10. The front wall 16 defines a centrally located tool-receiving opening 27 and a pair of fastener-receiving openings 28 disposed on opposite sides of the tool-receiving opening. The openings 27, 28 extend through the front wall 16 to the interior cavity 24. The tool-receiving opening 27, which may be threaded as illustrated, is configured to receive a suitable insertion tool for use in inserting the interbody spacer 10 in the patient. The tool-receiving opening 27 defines an opening axis A1 that extends generally parallel to the horizontal plane P of the spacer 10. The interbody spacer 10 may include other features for use with a suitable insertion tool. The fastener-receiving openings 28 define opening axes A2, A3 that extend at an angle to the horizontal plane P of the spacer 10. In the illustrated embodiment, axis A2 of a first fastener-receiving opening 28 is angled downward such that the axis extends through a bottom opening of the interior cavity 24, and axis A3 of a second fastener-receiving opening 28 is angled upward such that the axis extends through a top opening of the interior cavity. The fastener-receiving openings 28 are configured to receive a suitable fastener (such as fasteners 11) for use in securing the interbody spacer 10 in the patient. As will be described in greater detail below, fasteners 11 comprise curved nails/blades. However, any suitable fastener may be used. For example, a traditional bone screw 33 (FIG. 8) may also be used. Additionally, any combination of fasteners can be used without departing from the scope of disclosure. For example, a nail 11 could be inserted into the first fastener-receiving opening 28 (i.e., the left fastener opening in FIG. 1) and a bone screw 33 could be inserted in the second fastener-receiving opening 28 (i.e., the right fastener opening in FIG. 1). In this embodiment, the nail 11 would extend downward and the screw 33 would extend upward. Alternatively, the screw 33 could be inserted into the first fastener-receiving opening 28 and the nail 11 could be inserted in the second fastener-receiving opening 28.

Locking tabs 40 are formed in the fastener openings 28 and are configured to engage the fasteners 11 to prevent the fasteners from being pushed or pulled back out of the openings once the fasteners have been fully inserted into the openings. In the illustrated embodiment, each tab 40 is formed from the body of the spacer 10 and comprises a piece of material angled away from the material surrounding the fastener-receiving opening 28. Thus, the tabs 40 extend from the adjacent surrounding material and into the fastener-receiving openings 28. The tabs 40 are positioned within the openings 28 such that a base 60 of the fastener 11 will engage the tab as the fastener is being inserted into the opening and deflect the tab away from the opening 28 to allow for passage of the fastener. The tab 40 will then flex back to its pre-engaged position once the base 60 of the fastener 11 clears the tab thereby extending over the base of the fastener preventing the fastener from being withdrawn from the opening 28. The locking tab 40 may be broadly considered a blocking member such that the locking tab blocks the fastener 11 from being withdrawn from the fastener-receiving opening 28.

The material surrounding the fastener-receiving openings 28 also defines a fastener engagement portion 44 configured to seat the base 60 of the fastener 11 in the fastener-receiving opening once the fastener has been fully inserted into the opening. The fastener engagement portion 44 comprises a first angled section 46, a second angled section 48 extending at an angle from the first angled section, and a third angled section 50 extending at an angle from the second angled section. The third angled section 50 extends inward from the second angled section 48 to form a reduced diameter section of the fastener-receiving opening 28 which prevents the fastener 11 from being inserted entirely through and out of the bottom of the opening, as will be explained in greater detail below.

The upper and lower faces 20, 22 include rows of teeth 34. In the illustrated embodiment, there are two rows of teeth 34. Each row of teeth 34 extends between the front and rear walls 16, 18 and is located adjacent a respective side wall 12, 14. Thus, the first and second side walls 12, 14 are serrated at the upper and lower edge margins of the walls. The rows of teeth 34 facilitate anchoring of the interbody spacer 10 to the adjacent vertebrae within the interbody space to inhibit movement of the interbody spacer within the space. In other embodiments, the interbody spacer 10 may include other features to facilitate anchoring and inhibit movement of the interbody spacer within interbody space.

As shown in FIG. 1, each side wall 12, 14 further includes a three-dimensional lattice (i.e., 3D lattice), generally indicated at 52, disposed heightwise between the upper and lower surfaces 20, 22 and disposed widthwise between the front and rear walls 16, 18 (only the lattice on side wall 12 is shown). Solid frames 54 surround outer portions of the 3D lattices 52. Each 3D lattice 52 defines a plurality of intersecting passages extending therethrough. In this way, bone growth from vertebrae can enter the 3D lattice 52 and grow within the interconnected passages of the 3D lattice.

The interbody spacer 10 may be integrally formed as a one-piece monolithic component. For example, the entirety of the interbody spacer 10 may be formed by additive manufacturing, such as by direct metal laser sintering or by electron beam melting processes, as is generally known. The interbody spacer 10 may be formed entirely from a single type of metal, such as titanium, or the interbody spacer may comprise more than one type of metal. The interbody spacer 10 may also be formed in other ways. For example, the entirety of the interbody spacer 10 may be formed from 3D printing. During the 3D printing process, the interbody spacer 10 may be printed from the bottom of the spacer up to the top of the spacer, and from the back of the spacer to the front of the spacer. In the illustrated embodiment, the front wall 16 defines a front of the spacer 10.

Figure 3:
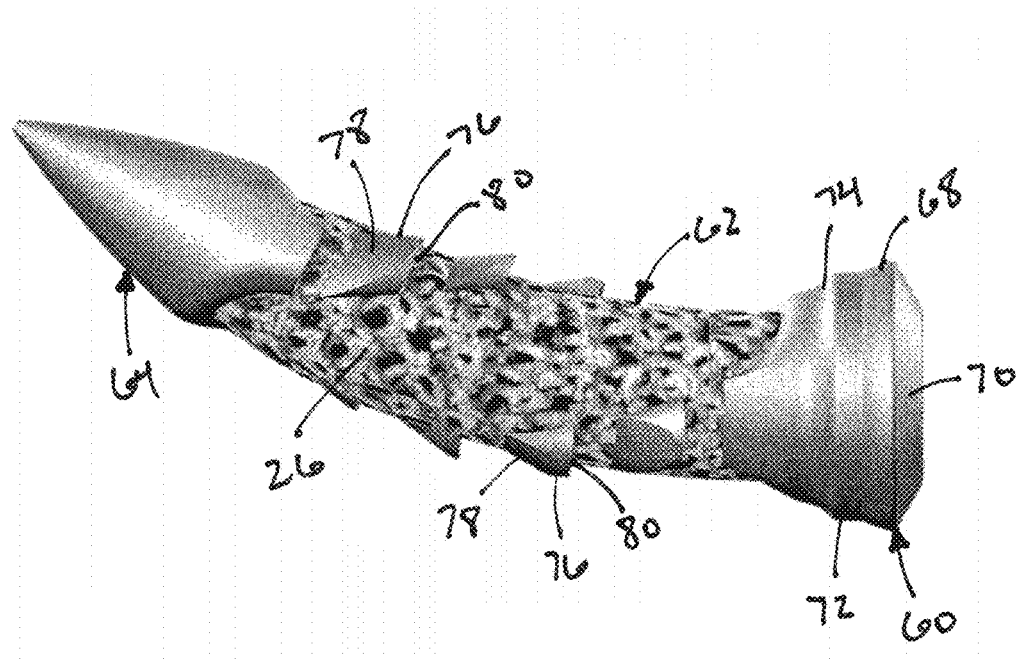
FIG. 3 is a perspective of a fastener of the interbody spacer assembly.
Figure 4:
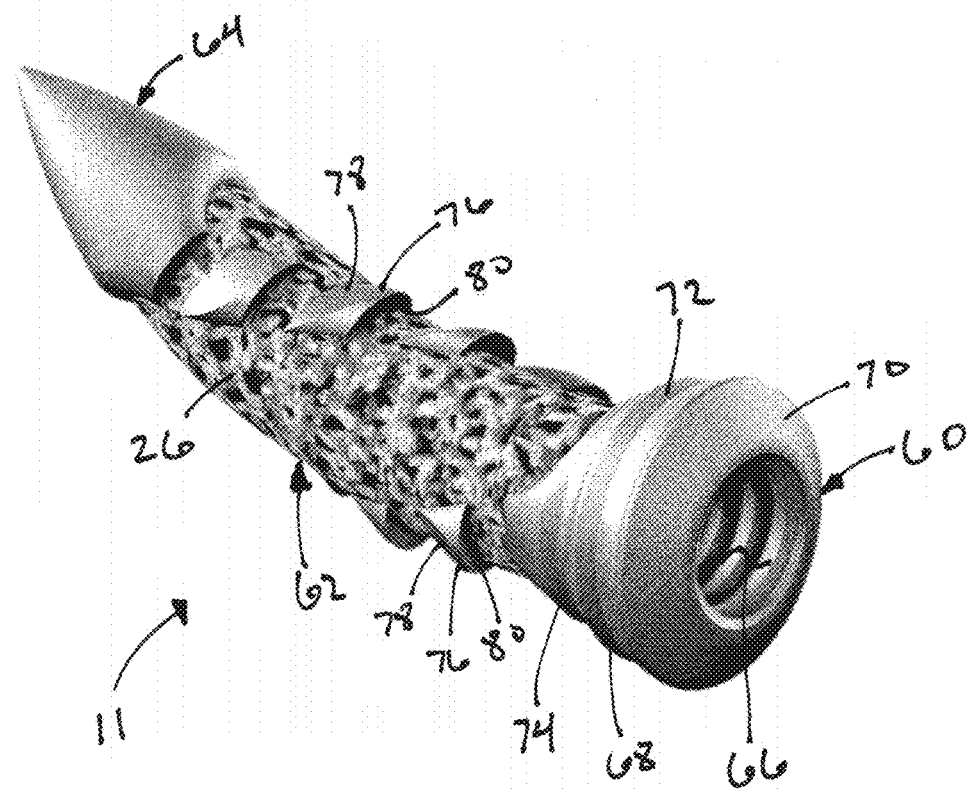
FIG. 4 is another perspective of the fastener.
Figure 5:
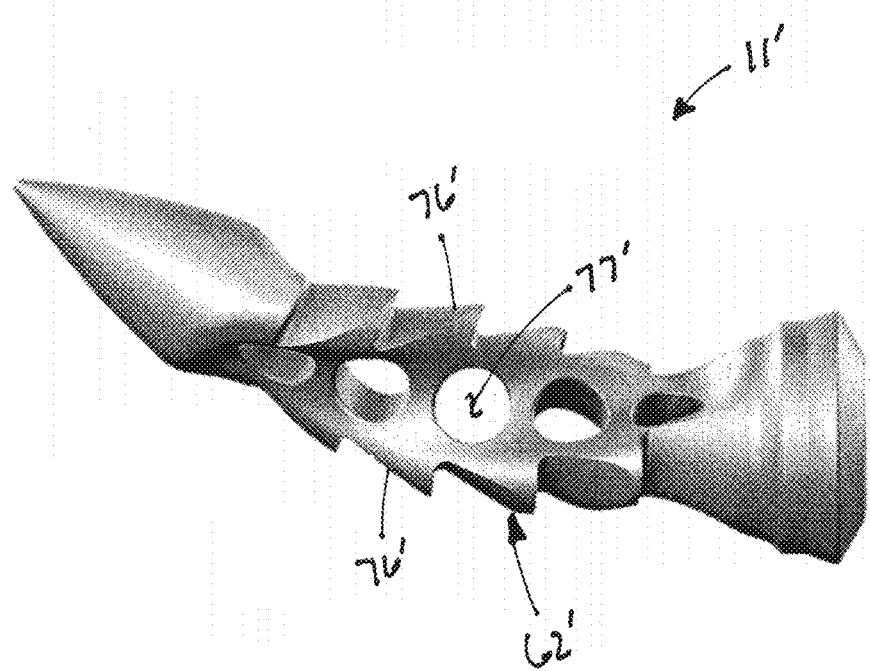
FIG. 5 is a perspective of another fastener.
Figure 6:
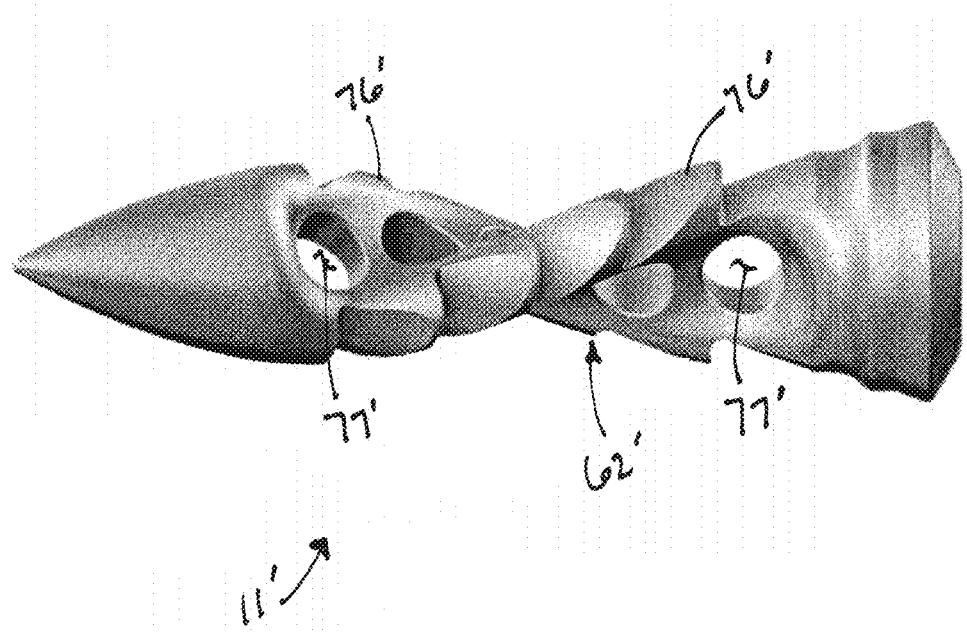
FIG. 6 is another perspective of the fastener of FIG. 5.
Figure 7A:
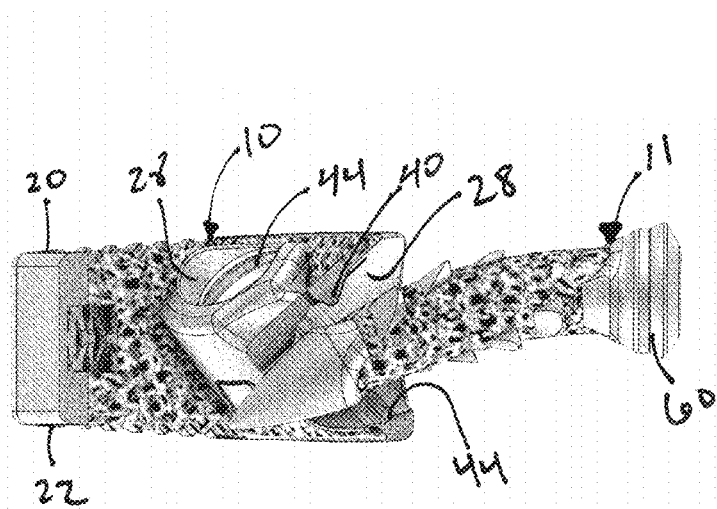
FIGS. 7A-7D are illustrations of fasteners being inserted into the interbody spacer.
Figure 7B:
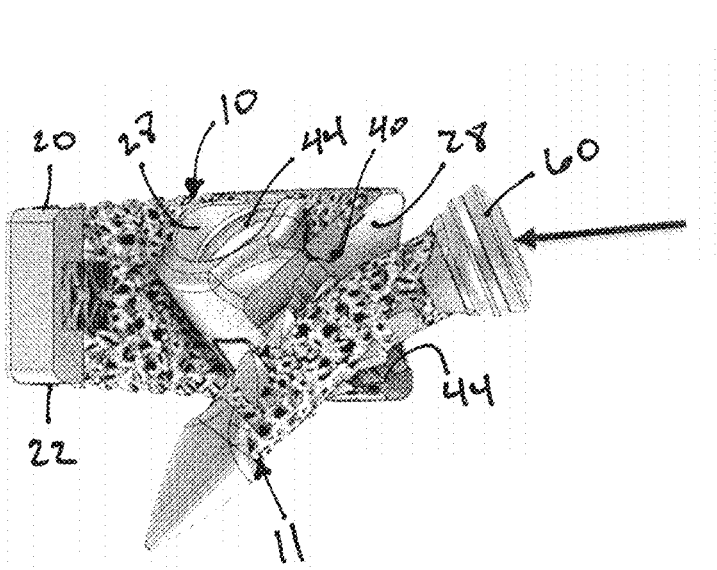
Figure 7C:
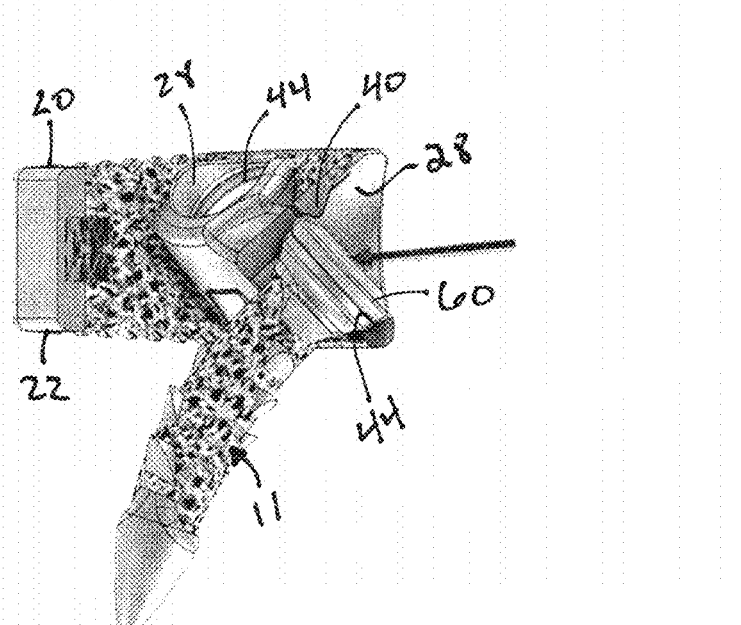
Figure 7D:
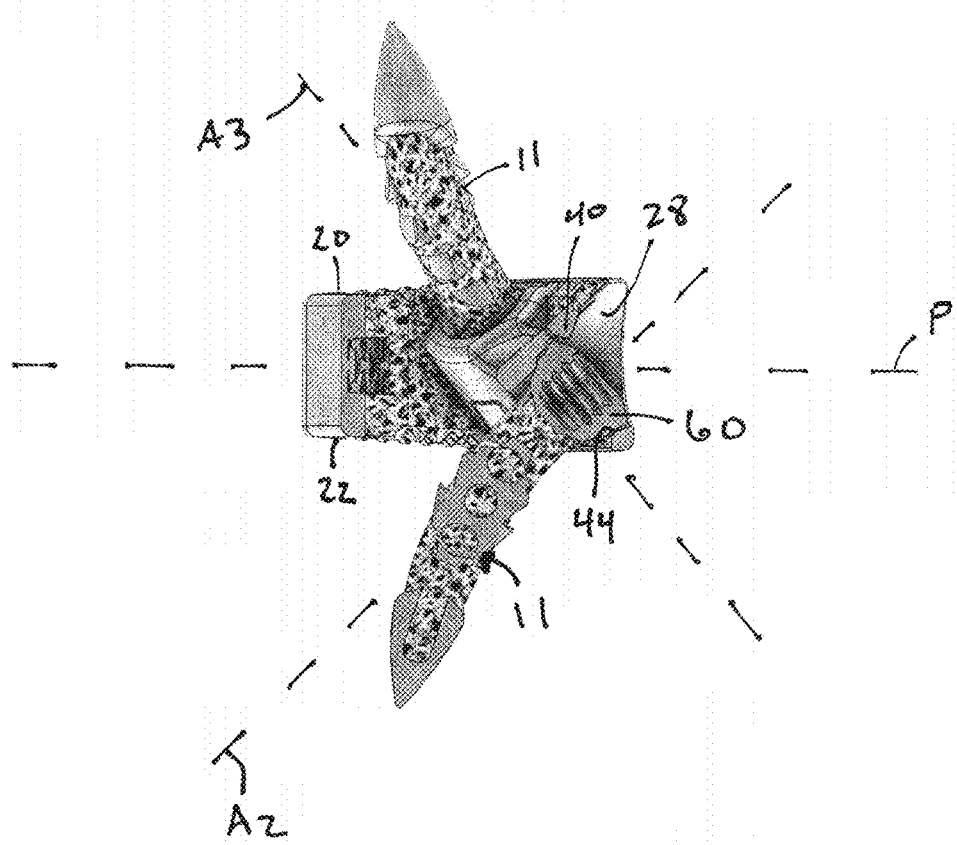

Referring to FIGS. 3 and 4, the fasteners 11 comprise curved trabecular nails/blades configured for insertion into a subject's bony structures (e.g., vertebrae). The nails 11 include a base 60, a shaft 62 extending from the base, and a tip portion 64 extending from the shaft. An inner surface of the base 60 defines a receptacle 66 for receiving a driver (not shown) for driving the nail into the bony structure. An outer circumferentially extending surface of the base 60 defines a unique contour for seating the base of the nail 11 in the fastener-receiving openings 28 of the spacer 10. In particular, the outer surface of the base 60 comprises a first angled section 68 extending from a rim 70 of the base, a second angled section 72 extending at an angle from the first angled section, and a third angled section 74 extending at an angle from the second angled section. The third angled section 74 of the base 60 is sized to engage the third angled section 50 of the fastener engagement portion 44 extending around the fastener-receiving openings 28 to seat the nail 11 in the opening. The shaft 62 comprises spirally extending teeth 76 that extend from the base 60 to the tip portion 64. In the illustrated embodiment, there are two rows of teeth 76. However, the shaft 62 could include additional rows of teeth without departing from the scope of the disclosure. Trabecular lattice 26 is disposed around the teeth 76 and similarly extends from the base 60 to the tip portion 64. At least a portion of each tooth 76 protrudes from the lattice 26 so that the teeth can be used to anchor the nail 11 in the bony structure. In particular, each tooth 76 included a forward cutting surface 78 for penetrating the bony structure, and a reward anti-retraction surface 80 for holding the nail 11 in the bony structure. The spiral arrangement of the teeth 76 also enhances the pullout strength of the nail 11. However, the nail could be straight without departing from the scope of the disclosure. The tip portion 64 comprises a smooth outer surface that tapers to a pointed end for piercing the bony structure. It is also envisioned that the nails 11 could have other configurations without departing from the scope of the disclosure. For example, the nails could have a similar configuration but with the trabecular lattice removed. This embodiment is shown as fastener 11' in FIGS. 5 and 6. Fastener 11' is identical to fastener 11 except for that the removal of the bone growth material exposes a helical shaft 62'. The helical shaft defines the two rows of spirally extending teeth 76' as well as a central row of holes 77'. This helical shaft also enhances the flexural strength of the nail in all directions (i.e. increased isotropy) as compared to a "non-twisted" configuration. The holes maximize internal porosity thereby providing additional areas for bone growth. The fastener 11' is otherwise constructed identically to fastener 11.

Referring to FIGS. 7A-D, in use, the interior cavity 24 may be packed with bone graft material and then inserted with an insertion tool within an interbody space between two adjacent vertebrae in a suitable surgical procedure such that the upper face 20 of the spacer 10 contacts the upper or superior vertebra and the lower face 22 of the spacer contacts the lower or inferior vertebra. In this position, the upper and lower teeth 34 anchor into the respective superior and inferior vertebrae. Next, the fasteners 11 can be inserted into the fastener-receiving openings 28 to anchor the spacer 10 to the superior and inferior vertebra. Fully inserting the fasteners 11 such that the base 60 of the fastener is seated on the fastener engagement portion 44 surrounding the fastener-receiving openings 28 will cause the locking tabs 40 to lock the fasteners in the openings preventing the fasteners from being withdrawn. After insertion of the spacer 10 and completion of the surgery, it is envisioned that bone from the adjacent vertebrae will grow into the trabecular lattice 26 in the interior cavity 24 and the 3D lattices 52 on the spacer. It is believed such bone growth into the interbody spacer 10 by way of the trabecular lattice 26 and the 3D lattices 52 promotes bone growth of the vertebrae and enhances fusion of the patient's spine, as is desired in such fusion surgery.

Referring to FIG. 9A-14, another embodiment of an interbody spacer assembly is generally indicated at reference numeral 101. The interbody spacer assembly 101 comprises an interbody spacer 110 and fasteners (i.e., bone screws) 33 for securing the spacer to one or more adjacent bony structures. This interbody spacer 110 is designed for use in lumbar interbody fusion surgery. This interbody spacer 110 is similar structurally to the interbody spacer 10. As such, the spacer 110 has essentially the same structural elements as spacer 10, which are indicated by corresponding reference numerals plus 100. Differences between interbody spacer 110 and interbody spacer 10 are discussed below.

One difference between interbody spacer 110 and interbody spacer 10 is that the tool-receiving opening 27 of spacer 10 is replaced with a blocking member opening 127 for receiving a blocking member 182 to block the fasteners 33 from being withdrawn from the fastener-receiving openings 128. Thus, the locking tabs 40 of spacer 10 are omitted from this embodiment and replaced with the blocking member 182. The blocking member opening 127 is generally positioned within the center of the spacer 110 between first and second side walls 112, 114. The blocking member opening 127 extends from the front wall 116 to an interior cavity 124 of the spacer 110. The blocking member opening 127 includes a first portion 184 that extends from the front wall 116 toward the interior cavity 124, and a second portion 186 that extends from the first portion to the interior cavity 124. The first portion 184 is defined by a funneled or conical surface that forms a reduced diameter section of the opening 127. The second portion 186 comprises a flared surface that extends from the funneled surface and widens the blocking member opening 127. A detent mechanism 188 is formed on an inner surface of the spacer 110 defining the interior cavity 124. The detent mechanism 188 comprises a pair of detents 190 including a ramp surface and a catch surface. The detents 190 are configured to engage the blocking member 182 to lock the blocking member in a locked position, as will be explained in greater detail below.

The blocking member 182 is configured to be received in the blocking member opening 127 and rotate in the opening to selectively place the blocking member in a locked (FIGS. 9A and 9B) and unlocked (FIGS. 10A and 10B) position. The blocking member 182 comprises a head 192 and a shaft 194 extending from the head. The head 192 has an elongate front face that has a generally Z or S like shape defining protrusions 195 at the ends of the head. A receptacle 196 is formed in the front face of the head 192 and is configured to receive a tool (not shown) for rotating the blocking member in the blocking member opening 127. A side surface 197 of the head 192 extends downward from the top surface, and a bottom surface 198 extends downward and tapers inward from the side surface. The bottom surface 198 has a mating profile with the funneled surface that defines the first portion 184 of the blocking member opening 127 so that the bottom surface can engage the funneled surface to seat the blocking member 182 in the blocking member opening. The funneled surface also extends laterally outward from the reduced diameter portion of the blocking member opening 127 thereby preventing the blocking member from falling out of the bottom of the blocking member opening. The shaft 194 of the blocking member generally flares outward as it extends away from the head 192 thereby progressively increasing a lateral dimension of the shaft. The lateral dimension of the shaft 194 increases such that at least a portion of the shaft is larger than the diameter of the reduced diameter portion of the blocking member opening 127. Therefore, the shaft 194 prevents the blocking member 182 from being pulled out of the top of the blocking member opening 127. A pair of wings 199 are formed on the shaft 194 and extend laterally outward from the shaft. The wings 199 are configured to engage the detents 190 to lock the blocking member 182 in the locked position. In one embodiment, the wings 199 provide a snap-fit engagement with the detent mechanism 188.

The blocking member opening 127 communicates with the fastener-receiving openings 128 such that rotation of the blocking member 182 in the blocking member opening causes at least portions of the head 192 to enter into the fastener-receiving openings. In particular, the head 192 of the blocking member 182 can be rotated to the unlocked position (FIGS. 10A and 10B) which clears the protrusions 195 on the head from the fastener-receiving openings 128 permitting the fasteners 33 to be inserted into the fastener-receiving openings. When the fasteners 33 are fully inserted, the head 192 can be rotated to the locked position (FIGS. 9A and 9B) so that the protrusions 195 on the head extend over the fastener-receiving openings 128 to block the fasteners from being withdrawn from the openings. Rotation of the head 192 to the locked position also causes the wings 199 on the shaft 194 to engage the ramp surfaces of the detents 190 and snap past the catch surfaces preventing the head from being rotated back to the unlocked position. Thus, the blocking member 182 provides a similar locking function to the locking tab 40 of spacer 10. Additionally, while the spacer 110 is shown as being used with screws 33, the spacer could be used with any suitable fastener such as nails 11 shown in FIG. 14. Still other suitable fasteners such as nails 11' are also envisioned.

The interbody spacer 110 may be integrally formed as a one-piece monolithic component. For example, the entirety of the interbody spacer 110 may be formed by additive manufacturing, such as by direct metal laser sintering or by electron beam melting processes, as is generally known. The interbody spacer 110 may be formed entirely from a single type of metal, such as titanium, or the interbody spacer may comprise more than one type of metal. The interbody spacer 110 may also be formed in other ways. For example, the entirety of the interbody spacer 110 may be formed from 3D printing. During the 3D printing process, the interbody spacer 110 may be printed from the bottom of the spacer up to the top of the spacer, and from the back of the spacer to the front of the spacer. In the illustrated embodiment, the front wall 116 defines a front of the spacer 10. The 3D printing process may be used to print the body of the spacer 110 and the blocking member 182 in the same printing session. For example, as the printer is printing the lines that includes the body of the spacer 110 and the blocking member 182, the gap between the spacer body and the blocking member will be filled with unmelted stock material in powder form that will eventually be removed providing the clearance necessary for the blocking member to move relative to the spacer body. Building from the bottom of the spacer 110 up to the top and from the back to the front facilitates 3D printing in this manner.

In use, the interbody spacer 110 may be implanted in the patient in a suitable manner. It is believed the interbody spacer 110 promotes bone ingrowth in the same manner as described above with respect to interbody spacer 10.

Referring to FIG. 15-21, another embodiment of an interbody spacer assembly is generally indicated at reference numeral 201. The interbody spacer assembly 201 comprises an interbody spacer 210 and fasteners 211 for securing the spacer to one or more adjacent bony structures. This interbody spacer 210 is designed for use in lumbar interbody fusion surgery. This interbody spacer 210 is similar structurally to the interbody spacer 10. As such, the spacer 210 has essentially the same structural elements as spacer 10, which are indicated by corresponding reference numerals plus 200. Also, the fasteners 211 are structurally similar to fasteners 11. As such, the fasteners 211 are indicated by corresponding reference numerals plus 200. Differences between interbody spacer 210 and interbody spacer 10, and the differences between the fasteners 211 and fasteners 11 are discussed below.

Referring to FIGS. 15 and 19A-21, one difference between interbody spacer 210 and interbody spacer 10 comprises the construction of locking tab 240. On interbody spacer 210, the locking tabs 240 comprise a first arm 241 extending generally longitudinally along an axis of the fastener-receiving opening 228, and a second arm 243 extending transversely from the first arm and into the fastener-receiving opening. The first arm 241 extends from a base of the arm that is directly attached to the material surrounding the fastener-receiving opening 228 to an end of the arm that is connected to the second arm 243. The second arm extends to a free end within the fastener-receiving opening 228. In the illustrated embodiment, the second arm 243 is angled back toward the base of the first arm 241. The tabs 240 are positioned within the openings 228 such that a base 260 of the fastener 211 will engage the tab as the fastener is being inserted into the opening and deflect the tab to allow for passage of the fastener. In particular, the first arm 241 will deflect away from the fastener-receiving opening 228 and into the interior space 224 of the spacer 210, and the second arm 243 will deflect away from the opening toward the first arm. This allows for the base 260 of the fastener 211 to clear the tab 240. The tab 240 will then flex back to its pre-engaged position once the base 260 of the fastener 211 clears the tab thereby extending over the base of the fastener preventing the fastener from being withdrawn from the opening 228. The locking tab 240 may be broadly considered a blocking member such that the locking tab blocks the fastener 211 from being withdrawn from the fastener-receiving opening 228.

Referring to FIGS. 16A-17C, one difference between the fastener 211 and fastener 11 concerns the construction of base 260 and its engagement with a driver 261. The fasteners 211 comprise curved trabecular nails/blades configured for insertion into a subject's bony structures (e.g., vertebrae). The nails 211 include a base 260, a shaft 262 extending from the base, and a tip portion 264 extending from the shaft. An inner surface of the base 260 defines a receptacle 266 for receiving a head 263 of the driver 261 for inserting the nail 211 into the fastener-receiving opening 228 and driving the nail into the bony structure. The receptacle 266 is defined by a slotted opening 267 which communicates with a rounded interior surface 269. In the illustrated embodiment, the interior surface 269 is free of threads. An outer circumferentially extending surface of the base 260 defines a unique contour for seating the base of the nail 211 in the fastener-receiving openings 228 of the spacer 210 similar to fastener 11. In addition, a rib 271 is formed on the outer surface of the base 260. The rib 271 is configured to be received in a notch 273 formed in the fastener-receiving opening 228 to prevent the fastener 211 from rotating once the fastener is fully inserted into the opening, as will be explained in greater detail below. It is also envisioned that the nails 211 could have other configurations without departing from the scope of the disclosure.

Figure 17A:
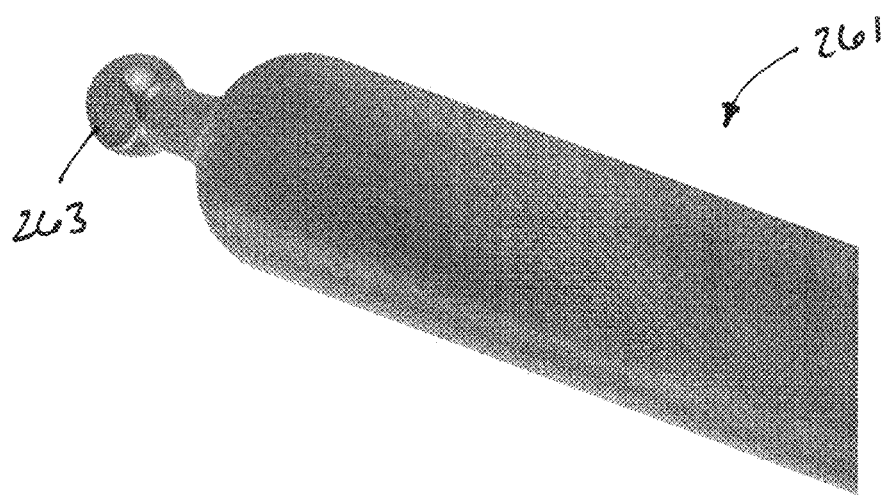
FIG. 17A is a fragmentary perspective of a driver.
Figure 17B:
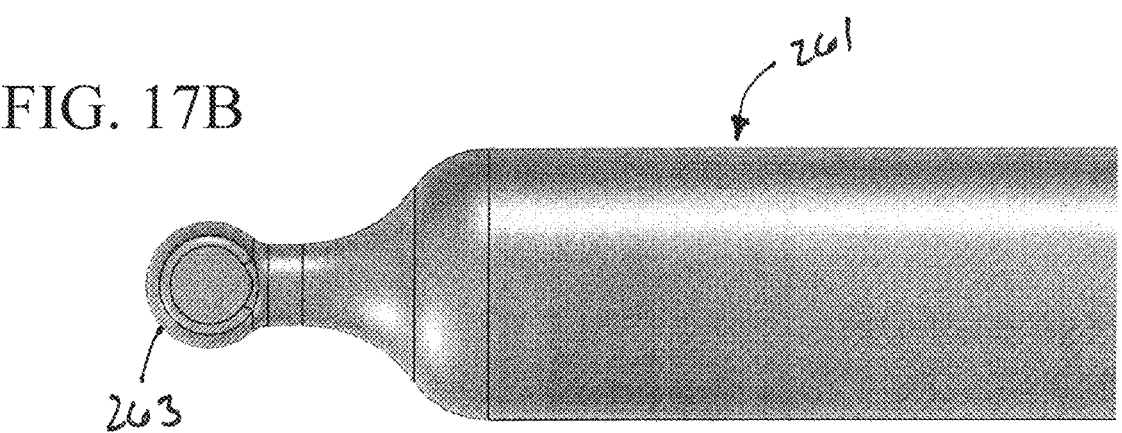
FIG. 17B is a front view of the driver of FIG. 17A.
Figure 17C:
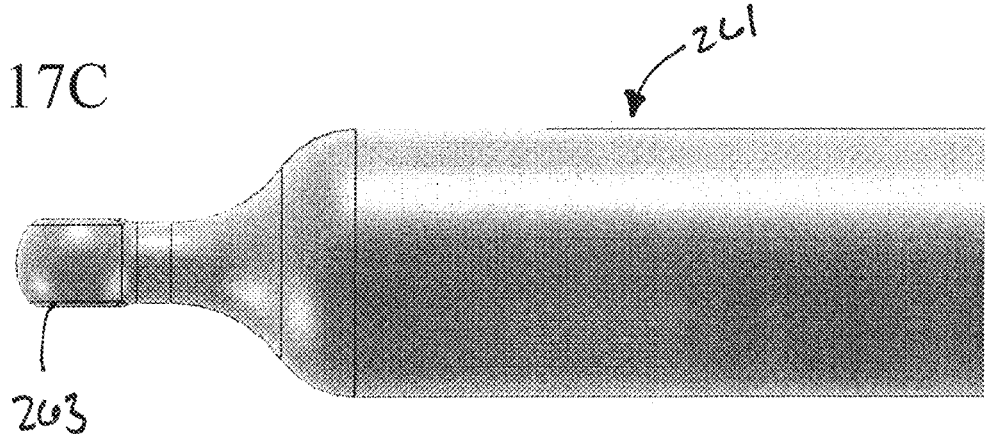
FIG. 17C is a top view of the driver of FIG. 17A.
Figure 18A:
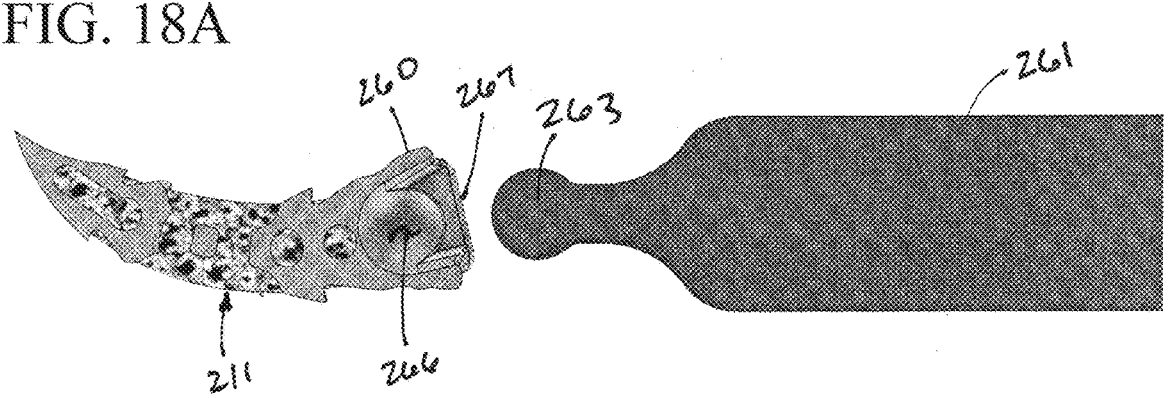
FIG. 18A-18C are illustrations of the driver being received in a base of the fastener of FIG. 16A.
Figure 18B:
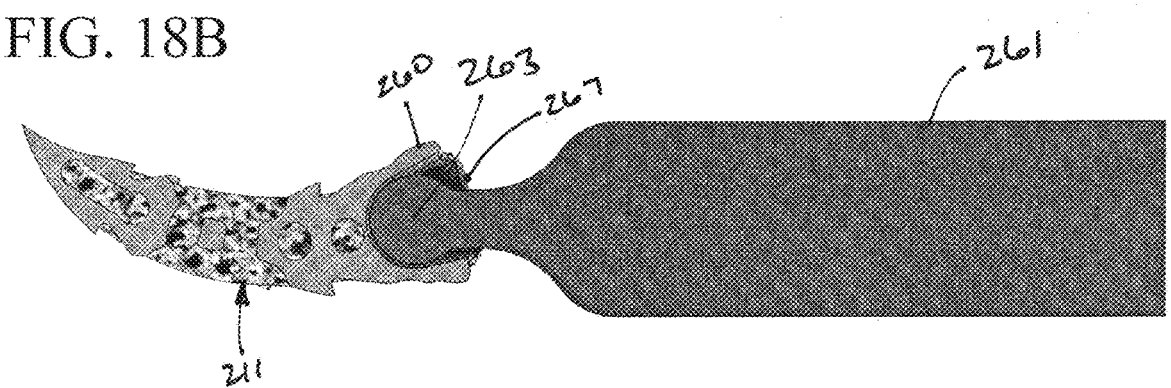
Figure 18C:
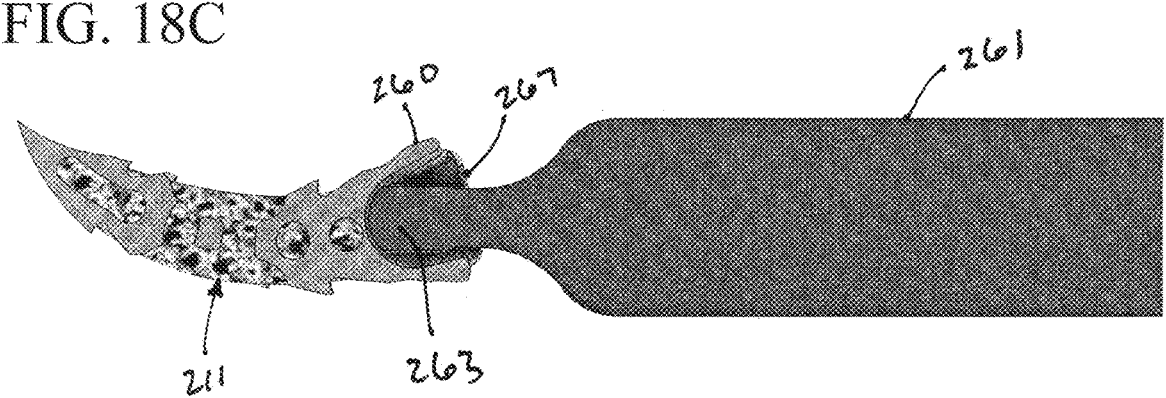
Figure 19A:
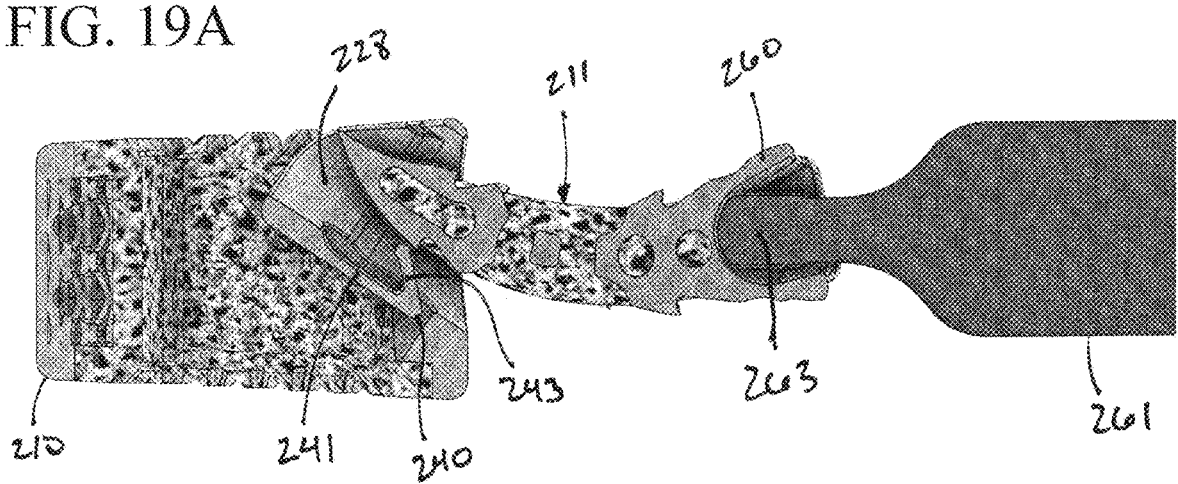
FIGS. 19A-19G are illustrations of the fastener of FIG. 16A being inserted into a spacer of the spacer assembly of FIG. 15.
Figure 19B:
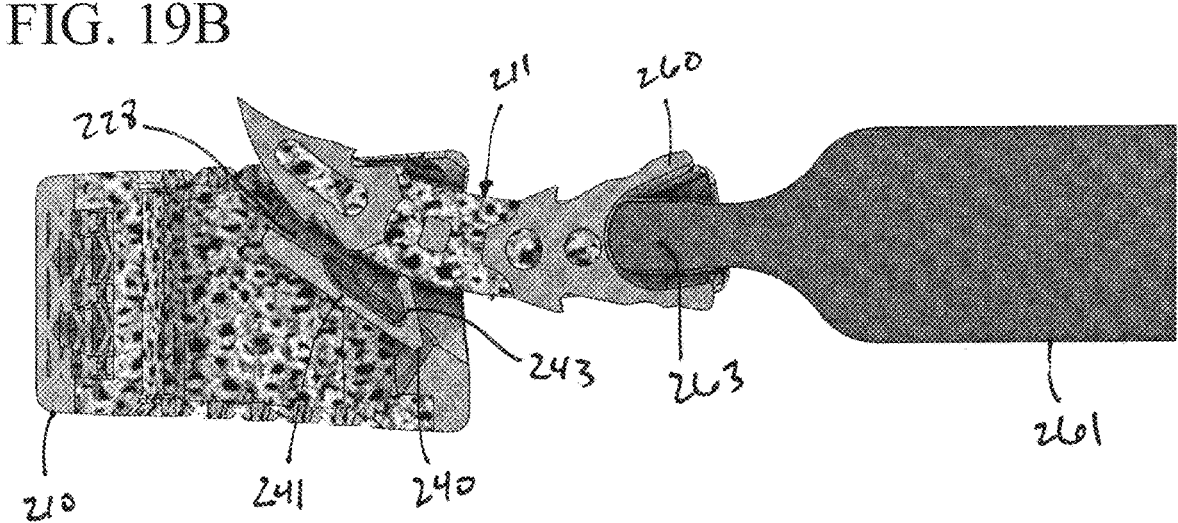
Figure 19C:
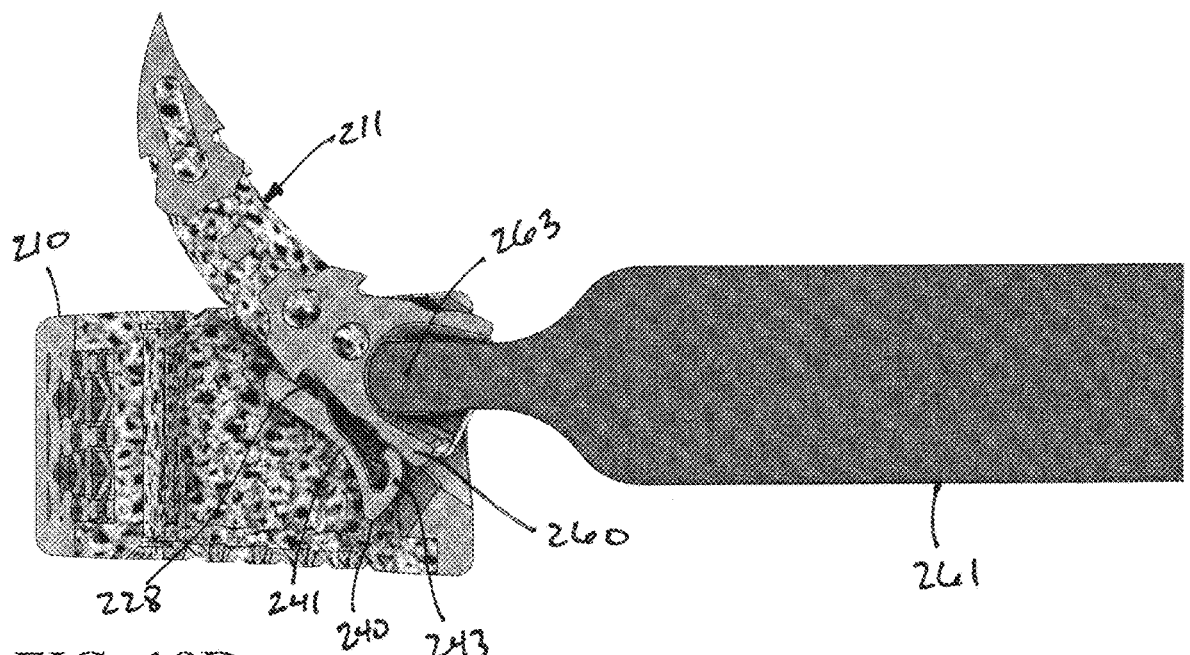
Figure 19D:
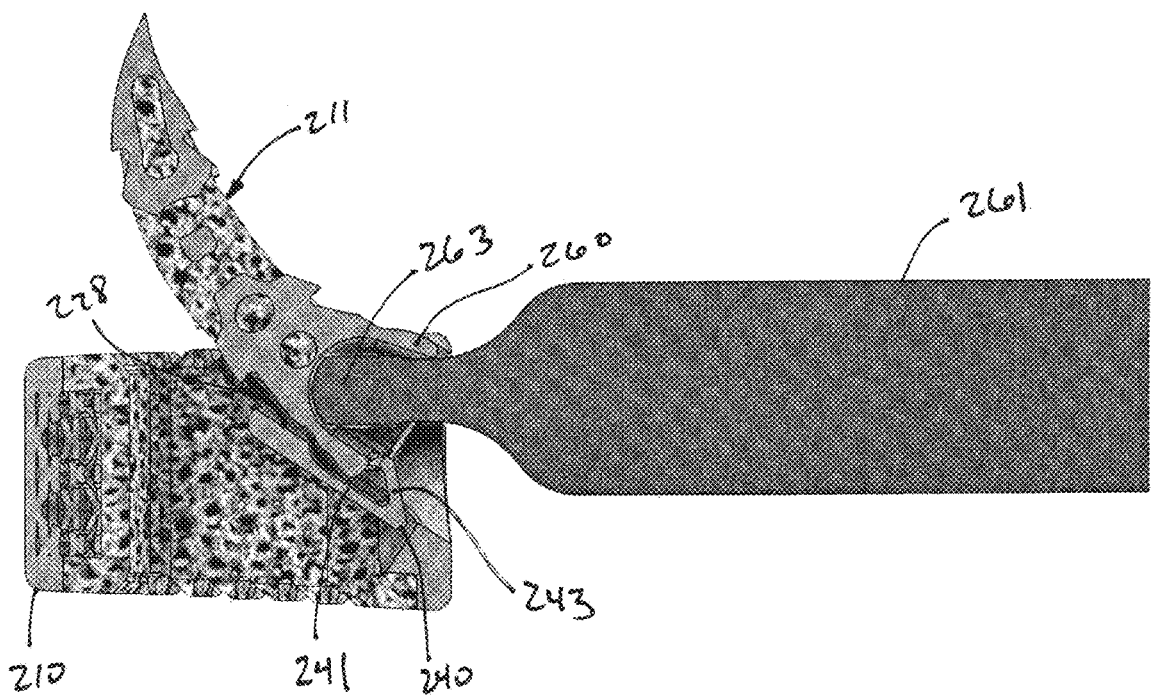
Figure 19E:
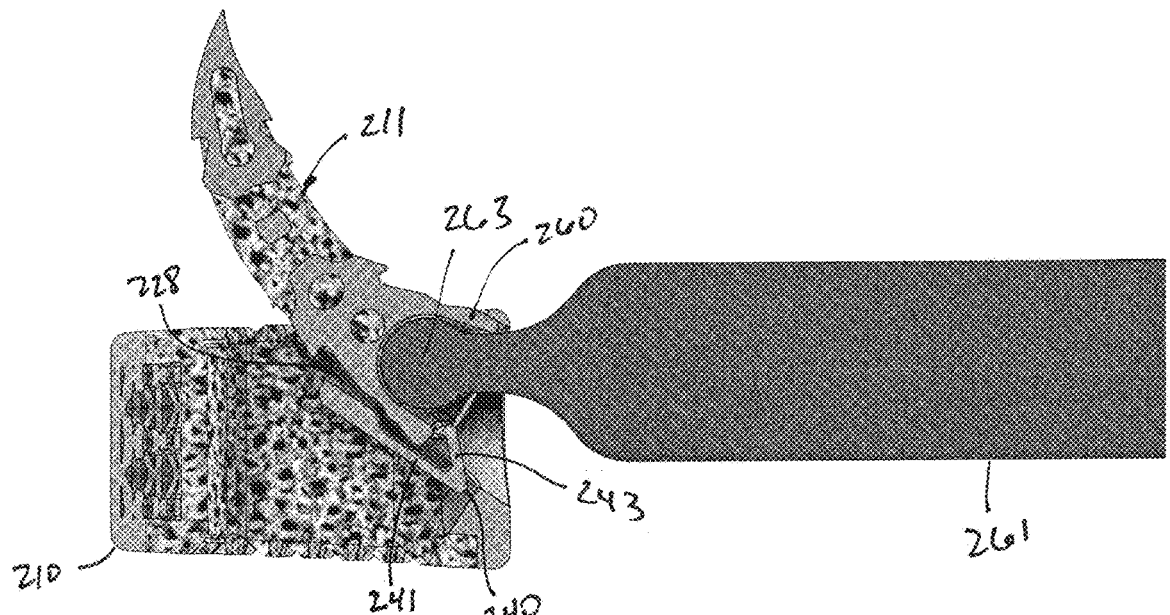
Figure 19F:
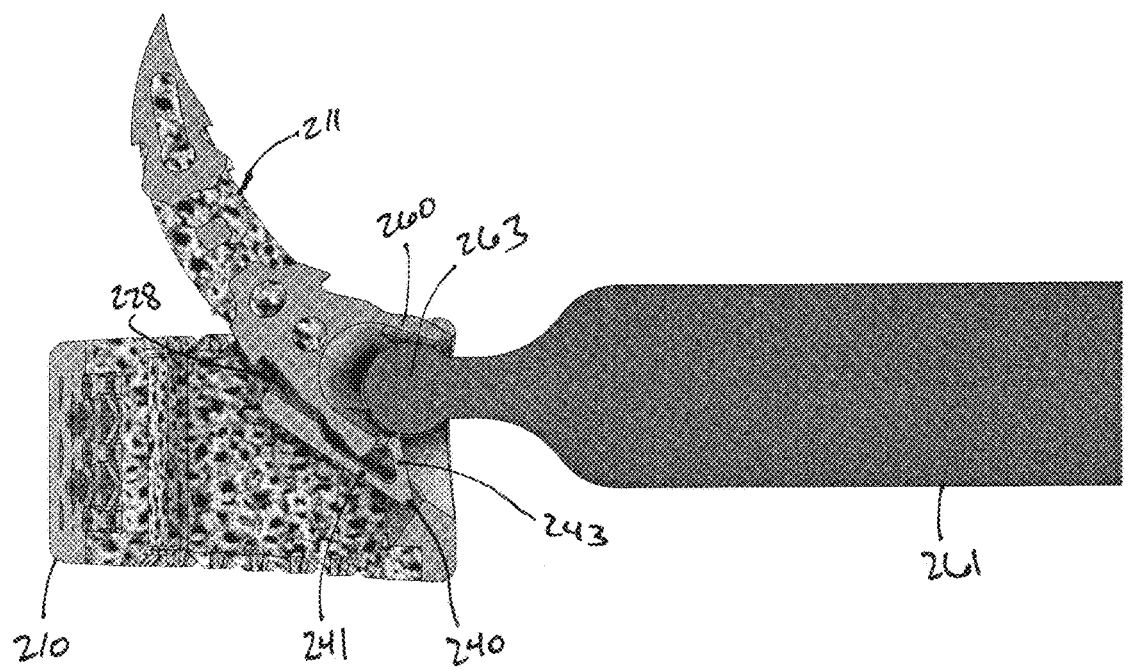
Figure 19G:
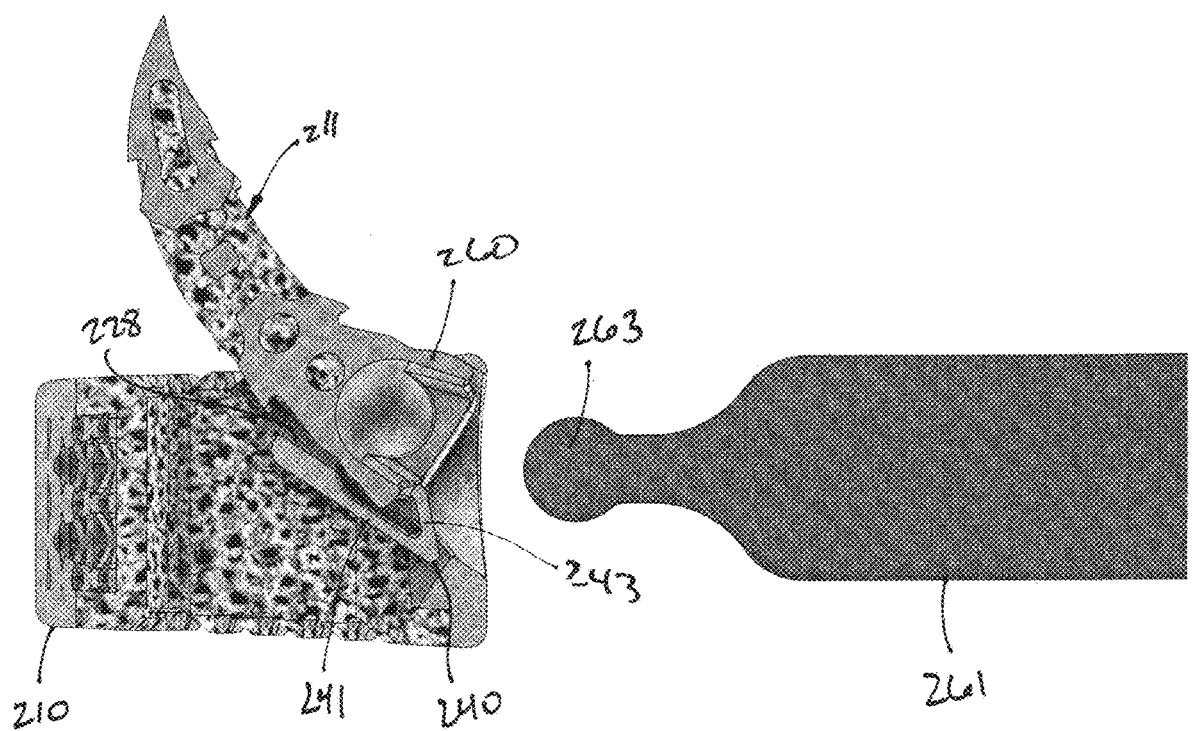

Referring to FIGS. 18A-19G, in use, the interior cavity 224 of the spacer 210 may be packed with bone graft material and then inserted with an insertion tool within an interbody space between two adjacent vertebrae in a suitable surgical procedure. Next, the fasteners 211 can be inserted into the fastener-receiving openings 228 to anchor the spacer 210. This can be done by aligning the head 263 of the driver 261 with the slotted opening 267 of the receptacle 266 in the head 260 of the fastener 211 and inserting the head of the driver into the receptacle. The head 263 of the driver 261 has a bulbous shape whereby a width of the head (FIG. 17B) is greater than a thickness of the head (FIG. 17C). Thus, the width dimension of the head 263 can be aligned along the length of the slotted opening 267 to insert the head of the driver 261 into the receptacle 266 (FIGS. 18A and 18B). The driver 261 is then rotated so that the width of the head 263 is misaligned with the length of the slotted opening 267 preventing the head from being withdrawn from the receptacle 266 (FIG. 18C). However, the head 263 of the driver 261 is still free to pivot or rotate within the receptacle 266 as there is no fixed connection between the head 263 and base 260 such as when a threaded connection is used.

Figure 20:
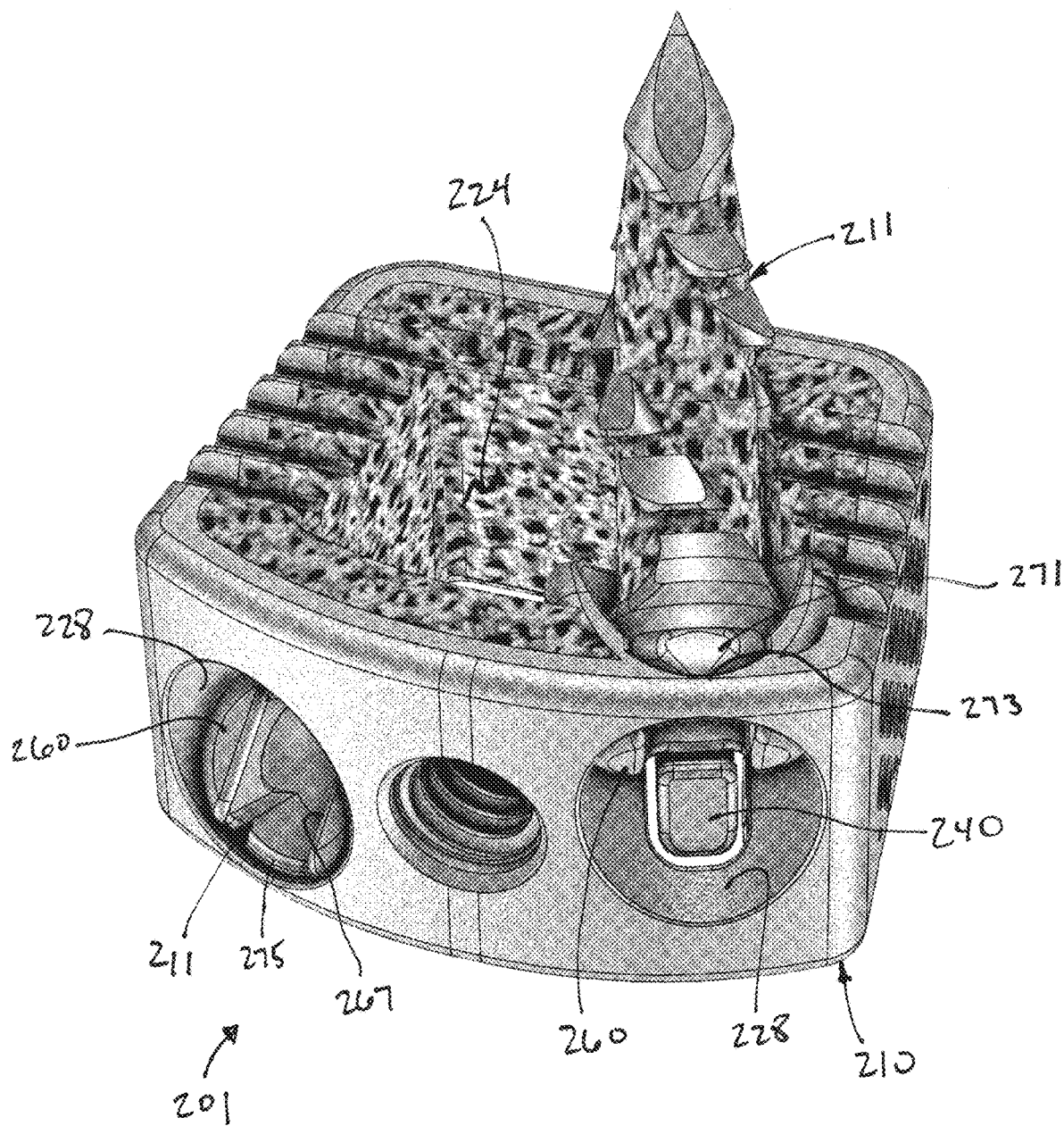
FIG. 20 is another front perspective of the interbody spacer assembly of FIG. 15.
Figure 21:
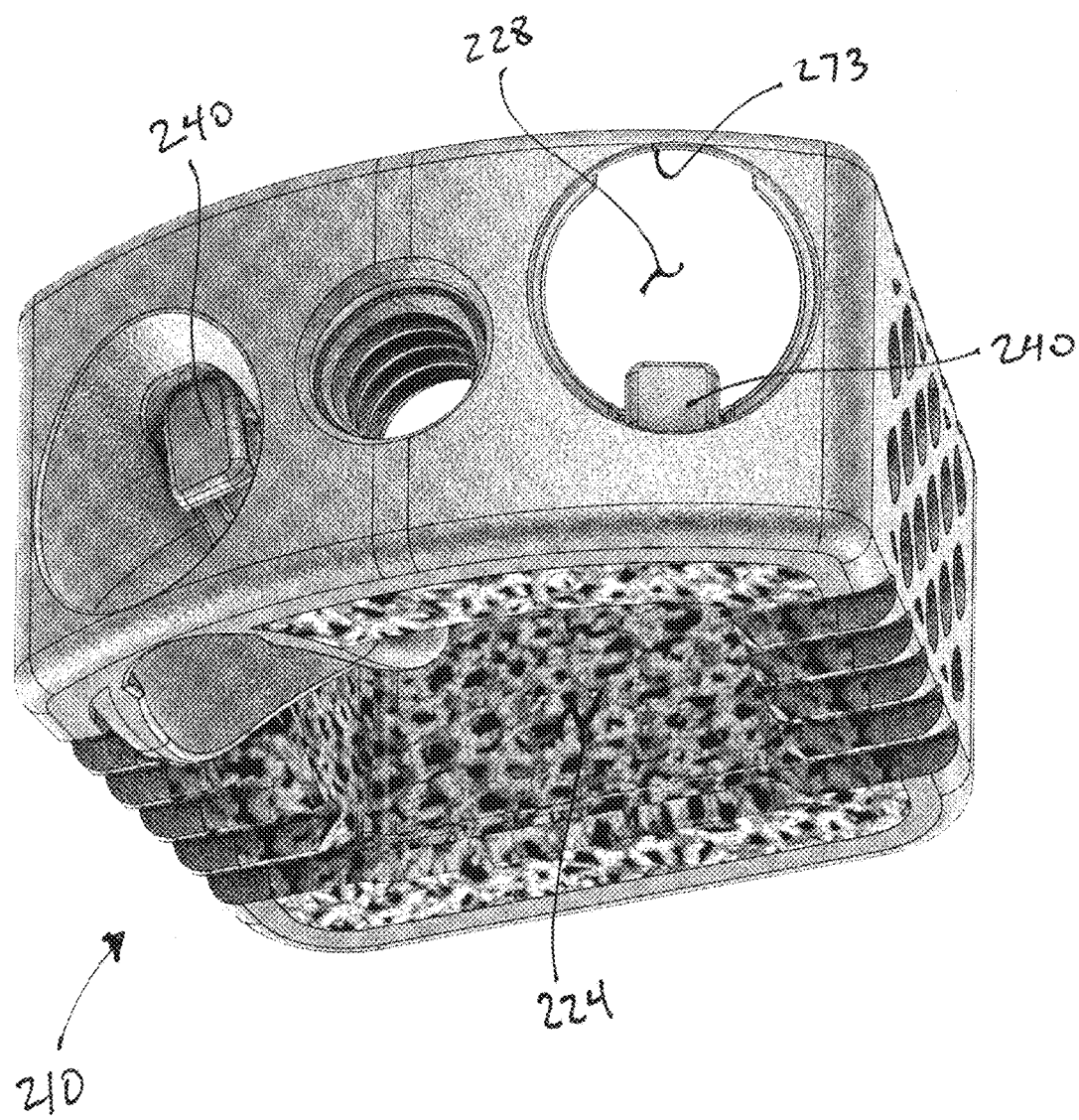
FIG. 21 is front perspective of the interbody spacer of the interbody spacer assembly of FIG. 15.

Referring to FIGS. 19A-19G, the driver 261 can then be used to insert the fastener 211 into the fastener-receiving opening 228. Because the head 263 of the driver 261 is free to pivot or rotate within the receptacle 266, the driver can be maintained generally at a position perpendicular to the subject's neck and spine as the curved fastener 211 is inserted into the fastener-receiving opening 228 along an arc. Fully inserting the fastener 211 will cause the locking tab 240 to lock the fastener in the opening 228 preventing the fastener from being withdrawn. Additionally, the rib 271 on the base 260 of the fastener 211 will be received in the notch 271 in the fastener-receiving opening 228 to prevent rotation of the fastener relative to the spacer 210 (FIGS. 20 and 21). The tab 240 is also received within a cutout 275 (FIGS. 16A and 16B) in the base 260 of the fastener 211 further preventing rotation of the fastener relative to the spacer 210. To decouple the driver 261 from the fastener 211, the driver is rotated to again align the width of the head 263 with the length of the slotted opening 267 permitting the head to be pulled out of the receptacle 266.

As used herein, "open-cell metal foam" and "trabecular lattice" refer to a porous structural component having a relatively roughened surface, an apparent randomized filament arrangement, and cell sizes and shapes forming an interconnected network or labyrinth to facilitate bone ingrowth.

As used herein, a "three-dimensional lattice" is a porous structural component including non-randomized, intersecting struts forming patterns of interconnected passages to facilitate bone growth.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A bone fastener comprising:
   a shaft having a length extending between proximal and distal ends of the shaft, wherein the shaft has an exterior surface;
   a base at the proximal end of the shaft and defining a receptacle configured to receive a head of a suitable driver for driving the bone fastener into bone;
   a tip portion at the distal end of the shaft and configured to bore into bone;
   anchoring projections extending laterally outward from the exterior surface of the shaft to a lateral outward end of the anchoring projection, wherein the anchoring projections are spaced apart from one another along the length of the shaft, wherein the anchoring projections are configured to enable anchoring of the bone fastener in bone; and
   open-cell metal foam disposed on an entirety of the exterior surface of the shaft, including between the anchoring projections, to enable bone growth, wherein the open-cell metal foam is spaced laterally inward of a lateral outward end margin of each of the anchoring projections such that the lateral outward end margin of each of the anchoring projections is exposed,
   wherein at least the lateral outward end margin of each and every one of the anchoring projections is not formed from the open-cell metal foam and is free from the open-cell metal foam being disposed thereon.

2. The bone fastener set forth in claim 1, wherein the bone fastener is integrally formed as a monolithic one-piece component by additive manufacturing.

3. The bone fastener set forth in claim 2, wherein the base head is not formed from the open-cell metal foam and is free from open-cell metal foam being disposed thereon.

4. The bone fastener set forth in claim 3, wherein the shaft defines a plurality of transverse openings.

5. The bone fastener set forth in claim 4, wherein the open-cell metal foam extends into the transverse openings.

6. The bone fastener set forth in claim 2, wherein the bone fastener is formed from titanium.

7. The bone fastener set forth in claim 2, wherein the tip of the bone fastener is not formed from the open-cell metal foam and is free from the open-cell metal foam being disposed thereon.

8. A method of making the bone fastener set forth in claim 1, the method comprising:
   additively manufacturing an entirety of the bone fastener.

9. The method of making the bone fastener set forth in claim 8, the method comprising:
   additively manufacturing an entirety of the bone fastener with titanium.

10. The bone fastener set forth in claim 1, wherein the anchoring projections comprise at least one thread.

11. The bone fastener set forth in claim 1, wherein the anchoring projections comprise teeth.

12. The bone fastener set forth in claim 1, wherein the shaft is straight.

13. The bone fastener set forth in claim 1, wherein the shaft is curved.

14. The bone fastener set forth in claim 1, wherein an entirety of the shaft is not formed from open-cell metal foam.

* * * * *